United States Patent [19]

Ramanathan

[11] 4,208,324
[45] Jun. 17, 1980

[54] DISPERSE DIAMINOPYRIDINE-3-AZO DYESTUFFS

[75] Inventor: Visvanathan Ramanathan, Basel, Switzerland

[73] Assignee: Ciba-Geigy Corporation, Ardsley, N.Y.

[21] Appl. No.: 922,708

[22] Filed: Jul. 7, 1978

Related U.S. Application Data

[63] Continuation of Ser. No. 737,137, Oct. 29, 1976, abandoned, which is a continuation of Ser. No. 602,165, Aug. 4, 1975, abandoned, which is a continuation of Ser. No. 457,882, Apr. 4, 1974, abandoned, which is a continuation-in-part of Ser. No. 314,487, Dec. 12, 1972, abandoned.

[30] Foreign Application Priority Data

Dec. 28, 1971 [CH] Switzerland ................... 19044/71
Apr. 11, 1973 [CH] Switzerland ..................... 5197/73

[51] Int. Cl.² ............................................. C09B 29/34
[52] U.S. Cl. .................................. 260/156; 260/153; 260/154; 260/155
[58] Field of Search ............... 260/153, 154, 155, 156

[56] References Cited

U.S. PATENT DOCUMENTS

| | | | |
|---|---|---|---|
| 2,068,353 | 1/1937 | Schneiderwrith | 260/156 |
| 2,145,579 | 1/1939 | Binz et al. | 260/156 |
| 2,148,705 | 2/1939 | Mietzsch et al. | 260/156 |
| 2,681,906 | 6/1954 | Granatek | 260/156 |

FOREIGN PATENT DOCUMENTS

| | | | |
|---|---|---|---|
| 2062717 | 6/1972 | Fed. Rep. of Germany | 260/156 |
| 270987 | 12/1950 | Switzerland | 260/156 |
| 1284879 | 8/1972 | United Kingdom . | |
| 1284880 | 8/1972 | United Kingdom . | |
| 1296857 | 11/1972 | United Kingdom . | |
| 1416738 | 12/1975 | United Kingdom . | |
| 1416740 | 12/1975 | United Kingdom . | |

Primary Examiner—Arthur P. Demers
Attorney, Agent, or Firm—Michael W. Glynn

[57] ABSTRACT

Azo dyes which are free from acid water-solubilizing groups and correspond to the formula

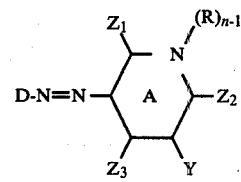

wherein two radicals Z represent groups of the formula —NR'R" and one of the radicals Z represent a group of the formulae —NR'R", OR'" or —S—R'", wherein R', R" and R'"each represents hydrogen, aryl, alkyl, aralkyl, cycloalkyl, an aliphatic or a heterocyclic radical and R' and R" are able to form a ring which contains the amino nitrogen, and the radicals —NR'R" may be the same or different, R is alkyl, substituted alkyl, cycloalkyl or substituted cycloalkyl, n is 1 or 2, Y represents a radical of the formulae —CN or —CONH$_2$, and D is the radical of an aromatic or heterocyclic diazo component; the nucleus A containing three double bonds if n is 1 and two double bonds if n is 2. The new dyestuffs dye polyester fibres in yellow and red shades.

20 Claims, No Drawings

DISPERSE DIAMINOPYRIDINE-3-AZO DYESTUFFS

This is a continuation of application Ser. No. 737,137, filed on Oct. 29, 1976, and now abandoned, which in turn is a continuation of application Ser. No. 602,165, filed Aug. 4, 1975, now abandoned, which in turn is a continuation of application Ser. No. 457,882 filed Apr. 4, 1974, now abandoned, which in turn is a continuation-in-part of application Ser. No. 314,487, filed Dec. 12, 1972, and now abandoned.

The present invention provides valuable new azo dyes which are free from water-solubilising groups, in particular from sulphonic acid groups, and which correspond to the general formula

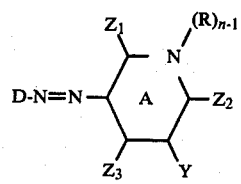

wherein two radicals Z represent groups of the formula —NR'R'' and one of the radicals Z represents a group of the formulae —NR'R'', —OR''' or —SR''', wherein R', R'' and R''' each represents hydrogen, aryl, alkyl, aralkyl, cycloalkyl or an aliphatic radical and R' and R'' are able to form a ring which contains the amino nitrogen, and the radicals —NR'R'' may be the same or different, R is alkyl, substituted alkyl, cycloalkyl or substituted cycloalkyl, n is 1 or 2, Y is the radical of the formulae —CN or —CO—NH$_2$, and D is the radical of an aromatic or heterocyclic diazo component; the nucleus A containing three double bonds if n=1 and two double bonds if n=2.

The dyestuffs are free from water-solubilising groups, such as anionic or cationic groups and belong to the class of disperse dyestuffs. Disperse dyestuffs are defined in the Colour Index. They are virtually insoluble in water and when aqueous dyeing baths are used, they must be applied as dispersions.

If n is one, the new dyestuffs correspond to the formula

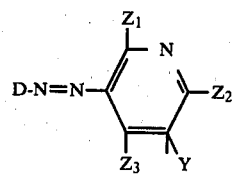

wherein two radicals Z represent groups of the formula —NR'R'' and one of the radicals Z represents a group of the formulae —NR'R'', OR''' or —S—R''', wherein R', R'' and R''' each represents hydrogen, aryl, alkyl, cycloalkyl or an aliphatic radical and R' and R'' are able to form a ring which contains the amino nitrogen, and the radicals —NR'R'' may be the same or different, Y represents a radical of the formula —CN or —CONH$_2$, and D is the radical of an aromatic or heterocyclic diazo component.

If n is two, the new dyestuffs correspond to the formula

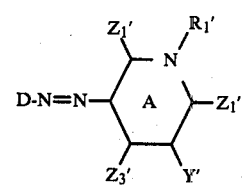

wherein $R_1'$ represents an optionally substituted alkyl, cycloalkyl, aralkyl, aryl, or heterocyclic radical, but preferably represents an optionally substituted alkyl or aralkyl radical or a cyclohexyl radical, $Z_1'$ represents a radical of the formulae =NH or —NH$_2$, $Z_2'$ represents a radical of the formulae =NR$_2'$, —NHR$_2'$, —NR$_3'$R$_4'$, —OR$_5'$ or —SR$_6'$, in which formulae $R_2'$, $R_3'$, and $R_4'$ each independently represents hydrogen atoms, optionally substituted alkyl, aralkyl, cycloalkyl, aryl or heterocyclic radicals, $R_3'$ and $R_4'$, together with the nitrogen atom to which they are bonded, are able to form a 5-membered or 6-membered ring, $R_5'$ represents a hydrogen atom, an alkyl radical, an aralkyl radical, a cycloalkyl radical, an aryl radical or a heterocyclic radical, $R_6'$ represents a hydrogen atom, an alkyl radical, an aralkyl radical, a cycloalkyl radical, an aryl radical or a heterocyclic radical, $Z_3'$ represents a radical of the formulae =NR$_1'$ or —NHR$_1'$, Y' represents a radical of the formulae —CONH$_2$ or, preferably, —CN, and D represents the radical of an aromatic or heterocyclic diazo component, and the dihydropyridine ring A' is substituted only be one doubly bonded nitrogen atom and contains two double bonds.

The dyestuffs wherein n is two constitute chemically homogeneous individuals, but they are subject to the laws of tautomerism.

The tautomerism can be illustrated as follows:

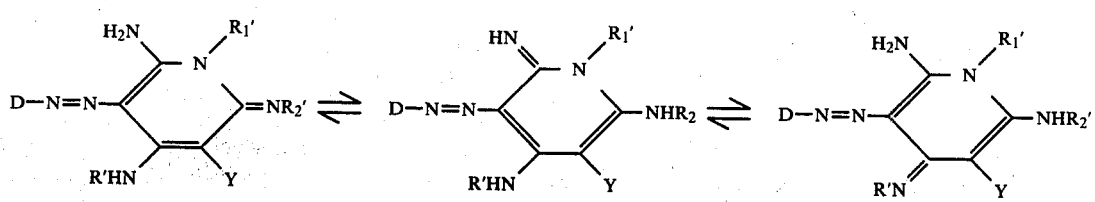

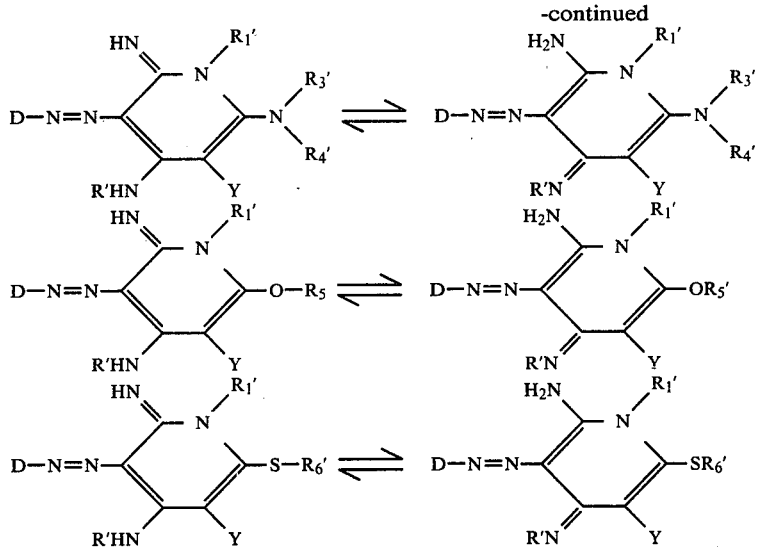

wherein $R_1'$, $R_2'$, $R_3'$, $R_4'$, $R_5'$, $R_6'$, Y and D have the same meanings as hereinbefore. The tautomeric dyestuffs illustrated hereinabove constitute prefered embodiments of the invention.

Dyes which also constitute a preferred embodiment of the invention are those of the formula

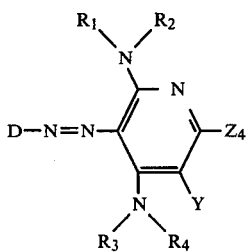

wherein $R_1$, $R_2$, $R_3$ and $R_4$ each represent hydrogen, an aryl, aralkyl, cycloalkyl or an aliphatic radical, it being possible for $R_1$ with $R_2$ and $R_3$ with $R_4$ to form a ring which contains the amino nitrogen, and wherein $Z_4$ represents a radical of the formula

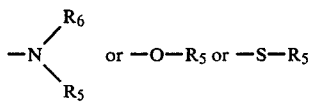

wherein $R_5$ and $R_6$ each represents hydrogen, aryl, aralkyl, cycloalkyl radicals or an aliphatic radical, and $R_5$ and $R_6$ can be linked to a heterocycle with contains the amino nitrogen, and, in particular, by dyes in which Y is a cyano group.

By aryl, aralkyl, cycloalkyl radicals and aliphatic radicals are meant preferably radicals of the benzene series, benzyl, phenethyl, cyclohexyl, or alkyl radicals with at most 12 carbon atoms, which last named radicals may be interrupted by oxygen or sulphur atoms or by imino groups. The radicals R at the same nitrogen atom may be linked directly with each other or through heteroatoms, in particular oxygen and sulphur, that is to say R' with R'', $R_1$ with $R_2$, $R_3$ with $R_4$ and, in particular, $R_5$ with $R_6$. The radical $Z_4$ can thus be, for example, a piperidine, pyrrolidine or morpholine radical. Suitable examples of the radicals R', R'', $R_1$, $R_3$, $R_4$, $R_5$ and $R_6$ are methyl, ethyl, propyl, isopropyl, butyl, sec.butyl, n-pentyl, and octyl radicals, which can be interrupted by oxygen atoms and substituted by hydroxy, carboxyl, carbalkoxy (with 2 to 6 carbon atoms), alkoxy (with 1 to 18 carbon atoms), phenoxy, acyloxy (with 1 to 10 carbon atoms), phenyl groups which are optionally substituted with halogen atoms, lower alkyl or lower alkoxy, β-hydroxyethyl or lower carboalkoxy groups, or phenyl or benzyl groups or phenethyl or cyclohexyl groups, or together are linked to a piperidine, pyrrolidine, morpholine, piperazine or methylpiperazine ring.

Possible acyl radicals are, for example, fatty acid radicals with up to 5 carbon atoms, such as formyl, acetyl, propionyl, butyl radicals; alkylcarbamyl radicals with up to 5 carbon atoms, such as methylaminocarbonyl, ethylaminocarbonyl, propylaminocarbonyl, or butylaminocarbonyl radicals; alkyloxycarbonyl radicals with up to 5 carbon atoms, such as methoxycarbonyl, ethoxycarbonyl, propoxycarbonyl or butoxycarbonyl radicals; phenylcarbamyl or phenoxycarbonyl radicals, benzoyl, phenoxyacetyl, chloroacetyl or phenylacetyl radicals.

Preferred dyes are those of the given formula in which D is a radical of the benzene series or a sulphur- and/or nitrogen-containing heterocyclic radical, as well as dyes in which $R_1$, $R_2$, $R_3$ and $R_4$ represent hydrogen.

The dyes are manufactured according to the invention by coupling a diazotised amine of the formula D—NH$_2$ with a coupling component of the formula

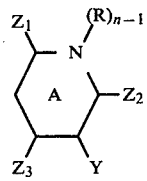

wherein two radical Z represent groups of the formula —NR'R'' and one of the radicals Z represents a group of the formulae —NR'R'', —OR''' or —SR''', wherein R', R'' and R''' each represents hydrogen, aryl, alkyl, aralkyl, cycloalkyl or an aliphatic radical and R' and R'' are able to form a ring which contains the amino nitrogen, and the radicals —NR'R'' may be the same or different, R is alkyl, substituted alkyl, cycloalkyl or substituted cycloalkyl, n is 1 or 2, Y is the radical of the formulae —CN or —CO—NH$_2$, and the nucleus A containing three double bonds if n=1 and two double bonds if n=2 and more especially by coupling with a coupling component of the formula

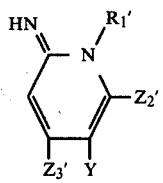

wherein R$_1'$, Z$_2'$, Z$_3'$ and Y are the same as defined above or by coupling with coupling components of the formulae

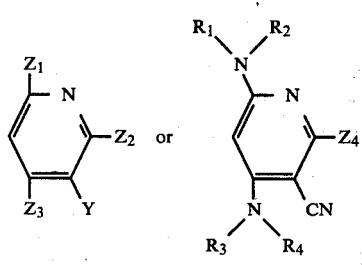

wherein D, Z$_1$, Z$_2$, Z$_3$, Z$_4$, R$_1$, R$_2$, R$_3$, R$_4$ and Y have the same meanings as hereinabove; and optionally, if Y=CN, converting the cyano group with concentrated sulphuric acid to the —CONH$_2$ group.

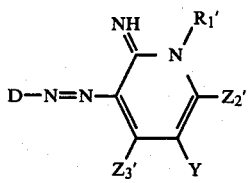

and by alkyl, aryl, aralkyl, cycloalkyl and heterocyclic radicals are meant preferably alkyl radicals which can be interrupted by oxygen or sulphur atoms or by groups of the formulae -NH- or -N-alkyl- or -N-aryl- and/or can carry substituents, radicals of the benzene series, optionally substituted benzyl, phenethyl, cyclohexyl radicals and radicals of the thiazole, benzthiazole, naphthothiazole, isothiazole, benzisothiazole, thiophene, imidazole, benzimidazole, thiadiazole, pyridine, quinoline, indazole, selenazole, oxazole, oxadiazole, benzoxazole, pyrazole, or triazole series.

The radicals R$_3'$ and R$_4'$ substituted at the same nitrogen atom can be bounded to each other direct or through heteroatoms, in particular oxygen and sulphur. The radical Z$_2$ can also be, for example, a piperidine, pyrrolidine, piperazine, morpholine, methylpiperazine, or an acetylpiperazine ring which is bonded to the pyridine ring through a nitrogen atom.

Suitable examples of radicals R$_1'$, R$_2'$, R$_3'$, R$_4'$, R$_5'$, and R$_6'$ are methyl, ethyl, propyl, isopropyl, butyl, sec. butyl, n-pentyl, and octyl radicals which can be interrupted by oxygen atoms and substituted by hydroxy, cyano, carboxy, acyloxy, acylamino, carbalkoxy (with 2 to 6 carbon atoms), alkoxy (with 1 to 10 carbon atoms), phenyl groups which are optionally substituted by halogen atoms, lower alkyl or lower alkoxy, β-hydroxyethyl, or lower carboalkoxy groups, or by benzyl or phenethyl or cyclohexyl groups.

Examples of acyl radicals which may occur in the radicals R$_1'$, R$_2'$, R$_3'$, R$_4'$, R$_5'$ and/or R$_6'$ are: fatty acids with up to 5 carbon atoms, e.g. formyl, acetyl, propionyl, butyl radicals: alkylcarbamyl radicals with up to 5 carbon atoms, e.g. methylaminocarbonyl, ethylaminocarbonyl, propylaminocarbonyl, or butylaminocarbonyl radicals; alkyloxycarbonyl radicals with up to 5 carbon atoms, e.g. methoxycarbonyl, ethoxycarbonyl, propoxycarbonyl, or butoxycarbonyl radicals; phenylcarbamyl or phenoxycarbonyl radicals, benzoyl, phenoxyacetyl, chloroacetyl, or phenylacetyl radicals. R$_1'$ is preferably a cyclohexyl radical or an optionally substituted alkyl or aralkyl radical.

If R$_1'$, R$_2'$, R$_3'$, R$_4'$, R$_5'$ and R$_6'$ represent aryl radicals, these are preferably an unsubstituted or mono- or polysubstituted phenyl radical which can be substituted by substituents of the following kind: halogen atoms, e.g. chlorine, bromine, fluorine, alkyl groups with 1 to 6 carbon atoms that in turn can be substituted by bromine, chlorine, lower alkoxy, cyano, or lower alkyloxycarbonyl groups, lower alkyloxycarbonyl, lower alkoxysulphonyl, trifluoromethyl, acetyl, aminocarbonyloxy, aminosulphonyl, lower alkylaminosulphonyl, di(lower alkylamino) sulphonyl, alkylsulphone, alkylthio, or arylthio radicals. Exemplary of such substituents at a phenyl radical are: the methyl, ethyl, propyl, butyl, isobutyl, or amyl group, a methoxy, an ethoxy, a propoxy or butoxy radical, a methoxymethyl, an ethoxymethyl, a β-methoxyethyl or an α-ethoxyethyl group, a (methoxy, ethoxy, propoxy)-methoxy or ethoxy group, methoxycarbonyl, ethoxycarbonyl, propoxycarbonyl group, the methoxy- or ethoxycarbonyl(methoxy or ethoxy) radical, a methoxycarbonylamino group, an ethoxycarbonylamino group, a methylsulphonyl or methylsulphinyl group, or a methyl, an ethyl, or a phenylthio radical. R$_5'$ is preferably an optionally substituted phenyl radical.

Preferred dyestuffs are those of the indicated formula in which D is a radical of the benzene series or is a heterocyclic radical which contains sulphur and/or nitrogen.

Preferably D represents a phenyl radical which is optionally substituted by halogen atoms, hydroxyl, cyano, thiocyano, nitro, lower alkyl trifluoromethyl, lower alkoxy, formyl, lower alkylcarbonyl, benzoyl, methylbenzoyl lower alkoxycarbonyl, benzoyloxycarbonyl, cyclohexyloxycarbonyl, phenoxycarbonyl, lower alkoxycarbonyloxy, benzoyloxycarbonyloxy, lower alkylcarbonyloxy, benzoyloxy, lower alkylcarbonylamino, benzoylamino, lower alkylsulphonyl, chloroethylsulphonyl, hydroxyethylsulphonyl groups, also by the following groups which are unsubstituted or mono- or disubstituted by lower alkyl groups: aminosulphonyl, di(hydroxyethyl)aminosulphonyl, phenylaminosulphonyl, (chloro- or methoxy)-phenylaminosulphonyl, benzylaminosulphonyl, N-piperidylsulphonyl, N-morpholinosulphonyl, lower alkylsulphonyloxy, cyclohexylsulphonyloxy, chloromethylsulphonyloxy, cyanoethylsulphonyloxy, phenylsulphonyloxy, aminosulphonyloxy, (chloro- or methoxy)phenylsulphonyloxy, N-morpholinosulphonyloxy, ethyleneiminosulphonyloxy, lower monoalkyl- or dialkylaminosulphonyloxy, phenylaminosulphonyloxy, N-phenyl-N(lower alkyl) aminosulphonyloxy, N-methoxy- or chloro)phenylaminosulphonyloxy, phenylamino, nitrophenylamino, dinitrophenylamino, phenyl, phenoxy; and/or by acetylaminophenyl groups; a phenylazophenyl radical which is optionally substituted by chlorine or bromine atoms, hydroxyl, cyano, nitro, lower alkyl, trifluoromethyl, lower alkoxy or phenoxy groups, a naphthyl radical which is optionally substituted by methoxy, ethoxy, phenylazo or dimethylaminosulphonyl groups, a thiazolyl radical which is optionally substituted by chlorine or bromine atoms, nitro, cyano, thiocyano, lower alkyl, lower alkoxy, lower alkylmercapto, phenyl, benzyl, phenethyl, lower alkoxycarbonyl, trifluoromethyl, lower alkylcarbonyl and lower alkylsulphonyl groups, a benzthiazolyl radical which is optionally substituted by chlorine or bromine atoms, cyano, thiocyano, nitro, lower alkyl, lower alkoxy, benzyl, phenethyl, lower alkylsulphonyl, phenyl, lower alkylmercapto, lower alkoxycarbonyl, lower alkylcarbonyl, trifluoromethyl, cyanoethylsulphonyl, aminosulphonyl groups, or a benzthiazolyl radical which is optionally mono- or disubstituted by dialkylaminosulphonyl groups, a pyrazolyl radical which is optionally substituted by cyano, lower alkyl, lower alkoxy, lower alkoxycarbonyl or phenyl groups, a thiadiazolyl radical which is optionally substituted by lower alkoxy, lower alkyl, phenyl, lower alkylsulphonyl or lower alkylmercapto groups, an imidazolyl radical which is optionally substituted by nitro or lower alkyl groups, a thienyl radical which is optionally substituted by nitro, lower alkyl, lower alkylsulphonyl, lower alkoxycarbonyl or acetyl groups, an isothiazolyl radical which is optionally substituted by lower alkyl, lower alkylsulfonyl, lower alkoxycarbonyl, nitro, cyano or phenyl groups, and a benzisothiazolyl radical which is optionally substituted by alkyl groups, nitro groups or halogen atoms. Lower alkyl groups are, for example, methyl, ethyl, propyl, isopropyl and isobutyl radicals; alkoxy radicals correspondingly contain from 1 to 4 carbons.

Preferably, the diazo radical D is derived from amines which contain a heterocyclic 5-membered ring with 2 or 3 heteroatoms, above all one nitrogen and one or two sulphur, oxygen or nitrogen atoms as heteroatoms, and aminobenzenes, primarily negatively substituted aminobenzenes in which the substituents have positive sigma values according to the Hammet equation, in particular those of the formula

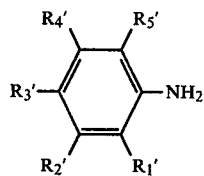

wherein $R_1'$ represents hydrogen, bromine, a thiocyano, alkylsulphonyl, alkoxycarbonyl, hydroxy, alkylmercapto, arylmercapto, alkoxycarbonyloxy, aminosulphonyloxy, acylamino group, or preferably chlorine, a nitro, cyano, acyl, sulphonamide, carboxylic acid amide, alkoxy or aryloxy group; $R_2'$ represents hydrogen, bromine, a carboxylic acid amide group or preferably an alkoxycarbonyl or aminosulphonyl group; $R_3'$ represents hydrogen, bromine, a thiocyano, alkoxycarbonyl, alkoxy, aryloxy or acylamino group, or preferably chlorine, or a nitro, cyano, acyl, sulphonamide, carboxylic acid amide, trifluoromethyl or phenylazo group, the phenyl nucleus of which in turn may be substituted with alkyl, alkoxy, or nitro groups and chlorine; $R_4'$ represents hydrogen, bromine, a nitro, cyano, thiocyano, acyl, carboxylic acid amide, alkoxy, aryloxy or acylamino group or preferably chlorine, a sulphonamide, alkoxycarbonyl, trifluoromethyl or alkyl group; $R_5'$ represents in particular hydrogen, chlorine or bromine, a nitro, cyano, thiocyano, acyl, alkoxycarbonyl, trifluoromethyl or an alkyl group.

In particular, $R_5'$ represents hydrogen, chlorine or bromine, a nitro, cyano, thiocyano, acyl, alkoxycarbonyl, trifluoromethyl or alkyl group.

Examples of such acyl radicals are: benzoyl, 4-chlorobenzoyl, 4-methylbenzoyl, benzenesulphonyl, formyl, acetyl, propionyl, chloroacetyl, methylsulphonyl or (methoxy, ethoxy, propoxy, butoxyoxy)carbonyl radicals.

From the series of useful diazo components of the benzene series the following may be mentioned as examples:

aniline,
1-amino-3- or -4-chlorobenzene,
1-amino-4-bromobenzene,
1-amino-2, -3- or -4-methylbenzene,
1-amino-2-, -3- or -4-nitrobenzene,
1-amino-4-cyanobenzene,
1-aminobenzene-3- or -4-methylsulphone,
1-amino-2-chlorobenzene-4-methylsulphone,
1-amino-2,5-dicyanobenzene,
1-amino-4-carbolthoxybenzene,
1-amino-2,4- or -2,5-dichlorobenzene,
1-amino-2,4-dibromobenzene,
1-amino-2-methyl-4- or -6-chlorobenzene,
4-aminodiphenyl,
2- or 4-aminodiphenylether,
3- or 4-aminophthalimide,
1-amino-2-trifluoromethyl-4-chlorobenzene,
1-amino-2-cyano-4-chlorobenzene,
1-amino-2-carbomethoxy-4-chlorobenzene,
1-amino-2-methylsulphonyl-4-chlorobenzene,
1-amino-2-carbomethoxy-4-nitrobenzene,
1-amino-2-phenoxy-4-nitrobenzene,
1-amino-2-chloro-4-cyanobenzene,
1-amino-2-chloro-4-nitrobenzene,
1-amino-2-methoxy-4-nitrobenzene,
1-amino-2-chloro-4-carboethoxybenzene,
1-amino-2-bromo-4-carbohexoxybenzene,
1-amino-2,4-dinitrobenzene,
1-amino-2,4-dicyanobenzene.
1-amino-2,6-dichloro-4-cyanobenzene,
1-amino-2,6-dichloro-4-nitrobenzene,
1-amino-2,5-dichloro-4-nitrobenzene,
1-amino-2,5- or 2,6-dichlorobenzene-4-sulphonic acid dimethylamide,
1-aminobenzene-4-sulphonic acid-β-chloroethylamide,
1-amino-2-chlorobenzene-4-sulphonic acid dimethylamide,
1-amino-2,6-dibromobenzene-4-sulphonic acid amide,
1-amino-2,4-dinitro-6-chloro- or -6-bromobenzene,
1-amino-2,4-dicyano-6-chlorobenzene,
1-amino-5-chloro-4-cyano-2-nitrobenzene,
1-amino-2,4,6-trichloro- or -tribromobenzene,
1-aminobenzene-3- or -4-sulphonic acid amide,
1-aminobenzene-3- or -4-sulphonic acid-N-methyl- or -diethylamide,
1-amino-2-nitrobenzene-4-sulphonic acid dimethylamide,
1-amino-2-nitrobenzene-4-ethylsulphone,
1-amino-4-nitrobenzene-2-methylsulphone, 1-aminobenzene-4-carboxylic acid-methoxyethyl ester,
1-amino-2-nitrobenzene-4-carboxylic acid ethoxyethyl ester,
1-amino-2-cyano-4-nitrobenzene,
1-amino-2-cyano-4-nitro-6-bromobenzene,
1-amino-2,6-dicyano-4-nitrobenzene,
1-amino-2-cyano-4,6-dinitrobenzene,
1-amino-2,4,5-trichlorobenzene.

Suitable aminobenzenes are the compounds of the formula

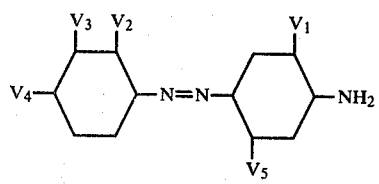

wherein $V_1$ represents a hydrogen atom, a halogen atom or a methyl, methoxy or ethoxy or nitro group, $V_2$ represents a hydrogen atom, a halogen atom or a nitro group, $V_3$ represents a hydrogen atom, a halogen atom or a nitro group, $V_4$ represents a hydrogen atom, a halogen atom, a methoxy, ethoxy, alkoxycarbonyl, cyano or nitro group, and $V_5$ represents a hydrogen atom, a halogen atom, a methyl or a methoxy group.

Examples of suitable diazo components of the azobenzene series are:
4-amino-azobenzene,
4-amino-2'-chloro-azobenzene,
4-amino-2',4'-dichloro-azobenzene,
4-amino-3'-chloro-azobenzene,
4-amino-2'-nitro-azobenzene,
4-amino-3-nitro-azobenzene,
4-amino-3'-nitro-azobenzene,
4-amino-2-methyl-azobenzene,
4-amino-4'-methoxy-azobenzene,
4-amino-3-nitro-2'-chloro-azobenzene,
4-amino-3-nitro-4'-chloro-azobenzene,
4-amino-3-nitro-2',4'-dichloro-azobenzene,
4-amino-3-nitro-4'-methoxy-azobenzene,
4-aminoazobenzene-4'-sulphonic acid dimethylamide and
4-amino-2-methylazobenzene-4'-carboxylic acid ethyl ester.

Suitable diazo components are also any kind of diazotisable, heterocyclic amines which do not contain any water-solubilising groups. These amines derive, for example, from the thiazole, benzthiazole, naphthothiazole, isothiazole, benzthiazole, thiophene, imidazole, benzimidazole, thiadiazole, pyridine, quinoline, indazole, selenazole, oxazole, oxadiazole, benzoxazole, pyrazole or triaxole series.

Possible substituents of these amines are: phenyl and phenylazo groups, it being possible for the phenyl rings to carry additional substituents, such as chlorine, nitro, alkyl, alkoxy and alkylmercapto radicals, each with 1 to 4 carbon atoms, halogen, in particular bromine and chlorine, sulphamoyl, trifluoromethyl, cyano, thiocyano, nitro, aralkyl, in particular benzyl, cycloalkyl, in particular cyclohexyl radicals, as well as alkyl, alkoxy, alkylmercapto, alkylsulphonyl, alkoxycarbonyl, alkanoyl and N,N-dialkylsulphonamide groups, in particular those radicals with 1 to 4 carbon atoms.

Preferred amines are those which have a heterocyclic 5-membered ring with 2 or 3 heteroatoms, chiefly one nitrogen and one or two sulphur, oxygen or nitrogen atoms as heteroatoms, i.e. in particular the amines of the thiazole, benzthiazole, isothiazole, benzisothiazole and thiadiazole series.

Preferred substituents of these amines are: halogen, especially chlorine or bromine, nitro, cyano, trifluoromethyl, alkyl and alkoxycarbonyl radicals, each with 1 to 4 carbon atoms, phenyl and the above cited substituted phenyl radicals. Examples of such heterocyclic diazo components are:
2-aminothiazole, 2-amino-5-nitrothiazole, 2-amino-5-methylsulphonylthiazole, 2-amino-5-cyanothiazole,
2-amino-4-methyl-5-nitrothiazole,
2-amino-4-methylthiazole,
2-amino-4-phenylthiazole,
2-amino-4-(4'-chloro)-phenylthiazole,
2-amino-4-(4'-nitro)-phenylthiazole,
3-aminopyridine,
3-aminoquinoline,
3-aminopyrazole,
5-amino-1-phenylpyrazole,
3-aminoindazole,
3-amino-2-methyl-5,7-dinitroindazole,
3-amino-1,2,4-triazole,
5-(methyl-, ethyl-, phenyl- or benzyl)-1,2,4-triazole,
3-amino-1-(4'methoxyphenyl)-pyrazole,
2-aminobenzthiazole,
2-amino-6-methylbenzthiazole,
2-amino-6-methoxybenzthiazole,
2-amino-6-chlorobenzthiazole,
2-amino-6-cyanobenzthiazole,
2-amino-6-nitrobenzthiazole,
2-amino-6-carboethoxybenzthiazole,
2-amino-6-methylsulphonylbenzthiazole,
2-amino-1,3,4-thiadiazole,
2-amino-1,3,5-thiadiazole,
2-amino-4-phenyl- or 4-methyl-1,3,5-thiadizole,
2-amino-5-phenyl-1,3,4-thiadiazole,
2-amino-3-nitro-5-methylsulphonyl-thiophene,
2-amino-3-nitro-5-acetylthiophene,
2-amino-3,5-bis-(methylsulphonyl)-thiophene,
5-amino-3-methyl-4-nitroisothiazole,
3-amino-5-nitro-2,1-benzisothiazole,
3-amino-7-bromo-5-nitro-2,1-benzisothiazole,
5-amino-4-nitro-1-methylimidazole,
4-amino-5-bromo-7-nitrobenzisothiazole,
4-amino-7-nitrobenztriazole.

The coupling component is preferably a 3-cyano-4,6-diaminopyridine which is substituted in the 2-position. The two amino groups are preferably not further substituted. Aliphatic and aromatic amino, oxy or mercapto groups are in the 2-position. These compounds can be manufactured by reacting 2-bromo-3-cyano-4,6-diaminopyridine with a primary or secondary amine, or a hydroxy or mercapto compound.

Examples of amines are: naphthylamine, aniline and derivatives thereof, such as 1-amino-3-chlorobenzene, 1-amino-4-carboethoxybenzene, 1-amino-2,4-dicyanobenzene, 1-amino-2-methoxy-4-nitrobenzene, 1-amino-2-methanesulphonyl-4-chlorobenzene, methylaminobenzene, ethylaminobenzene, 1-methylamino-3-chlorobenzene.

Primary and secondary aliphatic amines, such as methyl, ethyl, isopropyl, hexyl, octyl, decyl, methoxyethyl, isopropoxypropyl, dimethyl, diethyl, chloroethyl, ethanol, diethanol, propanol, benzyl or cyclohexylamine, morpholine, pyrrolidine and piperidine.

As alcohols there may be mentioned as examples: ethanol, propanol, isopropanol, butanol, 2-ethoxyethanol, cyclohexanol, benzylalcohol, phenol and the substituted derivatives thereof.

Examples of mercapto compounds are: ethyl mercaptan, thiophenol.

Preferred coupling components are those 3-carbonamido- or 3-cyano-4,6-diamino pyridines and 4-amino-6-imino- or 4-imino-6-amino-dihydropyridines which carry an amino group in the 2-position, in particular a morpholino, pyrrolidino or piperidino group.

The starting products, especially the diaminohalopyridines, are accessible e.g. according to Boldt et al., Angew. Chemie, vol. 82 (1970), page 392, W. J. Middleton, U.S. Pat. No. 2,790,806; Sasaki et al., Tetrahedron Letters 1971, page 4593 (cf. Yokoyama Bull. Chem. Soc. Japan, vol. 44 (1971), page 3195). Diamino halogenopyridinium chloride can be prepared according to A. L. Cossey, Angewandte Chemie, vol. 84 (1972), p. 1184.

The 3-cyano group can be converted by saponification in concentrated sulphuric acid into the 3-$CONH_2$ group.

Instead of a unitary diazo compound it is also possible to use a mixture of two or more of the diazo components according to the invention, and instead of a unitary azo component a mixture of two or more of the diazo components according to the invention, and instead of a unitary azo component, a mixture of two or more of the azo components according to the invention.

The diazotisation of the cited diazo components can be carried out by known methods, e.g. with the aid of mineral acid, in particular hydrochloric acid, and sodium nitrite, or e.g. with a solution of nitrosylsulphuric acid in concentrated sulphuric acid.

The coupling can also be carried out in known manner, for example in neutral to acid medium, optionally in the presence of sodium acetate or similar buffer substances which influence the rate of coupling, e.g. pyridine or its salts.

The new compounds, their mixtures with one another and their mixtures with other azo dyestuffs are excellently suitable for dyeing and printing leather, wool, silk, and above all, synthetic fibres such, for example, as acrylic or acrylonitrile fibres, polyacrylonitrile fibres and co-polymers of acrylonitrile and other vinyl compounds, such as acrylic esters, acrylic amides, vinyl pyridine, vinyl chloride or vinylidene chloride, co-polymers of dicyanoethylene and vinyl acetate, and of acrylonitrile block co-polymers, fibres of polyurethane, polyolefines, such as basically modified polypropylene, polypropylene modified with nickel or unmodified polypropylene, cellulose triacetate and cellulose 2½-acetate, and especially fibres of polyamides, such as nylon-6, nylon-6,6 or nylon-12, and of aromatic polyesters, such as those from terephthalic acid and ethylene glycol or 1,4-dimethylcyclohexane and co-polymers of terephtthalic acid and isoterephthalic acid with ethylene gylcol.

The dyeing of the above-mentioned fibre materials with the azo dyestuffs according to the invention that are sparingly soluble in water, is carried out preferably from aqueous dispersions. If the dyestuffs of the invention contain hydrophilic groups, e.g. one or more hydroxyalkyl, carboxylic amide or sulphonamide groups in the diazo component, they are best applied from a solvent liquor. It is appropriate, therefore, to finely divide the representatives suitable for use as disperse dyestuffs by grinding them with textile auxiliaries such, for example, as dispersants, and possibly with other grinding auxiliaries. By subsequent drying, dyestuff preparations are obtained consisting of textile auxiliary and the dyestuff.

Examples of dispersants of the non-ionic groups that can be used with advantage are: addition products of 8 mols of ethylene oxide with 1 mol of p-tert.-octylphenol, of 15 resp. 6 mols of ethylene oxide with castor oil, of 20 mols of ethylene oxide with the alcohol $C_{16}M_{33}OH$, ethylene oxide addition products with di-[α-phenylethyl]-phenols, polyethylene oxide-tert.-dodecyl-thioether, polyamine-polyglycol ether or addition products of 15 or 30 mols of ethylene oxide with 1 mol of the amino $C_{12}H_{25}MH_2$ or $C_{18}H_{37}NH_2$.

As anionic dispersants there may be mentioned: sulphuric acid esters of alcohols of the fatty series having 8 to 20 carbon atoms, of the ethyleneoxy adducts of the corresponding fatty acid amides, or of alkylated phenols having 8 to 12 carbon atoms in the alkyl radical: sulphonic acid esters with alkyl radicals having 8 to 20 carbon atoms; sulphation products of unsaturated fats and oils; phosphoric acid esters having 8 to 20 carbon atoms; fatty acid soaps also alkylaryl sulphonates, condensation products of formaldehyde with naphthalenesulphonic acid and lignin sulphonate.

Suitable cationic dispersants are quaternary ammonium compounds that contain alkyl or aralkyl radicals having 8 to 20 carbon atoms.

In addition to the dispersants, the dyestuff preparations can contain organic solvents, especially solvents that boil above 100° C. and preferably are miscible with water, such as mono- and dialkylglycol ether, dioxane, dimethylformamide or dimethylacetamide, tetramethylenesulphone or dimethylsulphoxide. Dyestuff, dispersant and solvent can with advantage be ground with one another.

The polyester fibres are dyed from aqueous dispersion with the dyestuffs according to the invention, which are sparingly soluble in water, according to the conventional processes for polyester materials. Polyesters of aromatic polycarboxylic acids with polyhydric alcohol are dyed preferably at temperatures of over 100° C. under pressure. However, the dyeing can also be carried out at the boiling point of the dyed bath in the presence of dyestuff carriers, for example phenylphenols, polychlorobenzene compounds or similar auxiliaries, or according to the thermosol process, that is to say padding with subsequent after-treatment with the application of heat, for example thermosetting, at 180°-210° C. Cellulose 2½-acetate fibres are dyed preferably at temperatures of 80°-85° C., whereas cellulose triacetate fibres are dyed advantageously at the boiling point of the dye bath. The use of dyestuff carriers is superfluous in dyeing cellulose 2½-acetate or polyamide fibres. Anthraquinone dyestuffs according to the invention can also be used for printing the cited materials according to conventional methods.

The dyeings obtained according to the instant process can be subjected to an after-treatment, for example by heating with an aqueous solution of an ion-free detergent.

According to the process of the present invention, the cited compounds can also be applied by printing instead of by impregnating. To this end, a printing ink, for example, is used which contains the finely dispersed dyestuff in addition to the usual auxiliaries used in the printing industra, such as wetting agents and binders.

Furthermore, it is possible to dye, for example, synthetic fibres, such as polyesters and polyamides in organic solvent liquors, such as a mixture of perchloroethylene and dimethylformamide or in pure perchloroethylene.

According to the process of the present invention, full dyeings and prints possessing good fastness properties are obtained, especially good fastness to thermosetting, sublimation, pleating, exhaust gas, cross-dyeing, dry-cleaning and chlorine, and good wet fastness properties, for example fastness to water, washing and perspiration.

It is also possible to use the new water-insoluble compounds for the spin dyeing of polyamides, polyesters and polyolefines. The polymers to be dyed are appropriately in the form of powder, grains or chips, as ready prepared spinning solution or mixed in the fused state with the dyestuff, which is introduced in the dry state or in the form of a dispersion or solution in an optionally volatile solvent. After the dyestuff has been uniformly distributed in the solution or the melt of the polymer, the mixture is processed in known manner by pouring, moulding or extruding to fibres, yarns, monofilaments, films and the like.

The following Examples illustrate the invention, the parts and percentages being by weight unless otherwise stated.

INSTRUCTION 1

10.65 parts of 2-bromo-3-cyano-4,6-diaminopyrdine, 10 parts of alcohol and 16 parts of 70% aqueous ethylamine are heated for 4 hours in an autoclave at 100° C. Excess amine and the other volatile constituents are evaporated in vacuo and the residue, which contains the compound of the formula

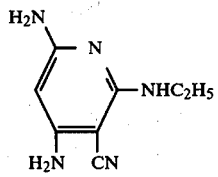

is used as coupling component without further purification. Recrystallization from alcohol yields the pyridine derivative as a yellow powder.

INSTRUCTION 2

10.65 parts of 2-bromo-3-cyano-4,6-diaminopyridine and 24 parts of aniline are heated for 4 hours at 140° C. The mixture is cooled, adjusted to pH 7 to 8 with sodium hydroxide solution, and excess aniline is expelled with steam. The precipitated yellow powder (m.p. 147° C.) of the formula

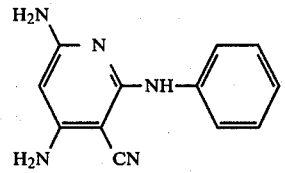

is isolated and used as coupling component without further purification.

INSTRUCTION 3

4.26 parts of 2-bromo-3-cyano-4,6-diaminopyridine are dissolved hot in 120 parts of methyl alcohol. 3 parts of sodium methylate are added and the mixture is boiled under reflux until no more starting substance can be detected in a thin-layer chromatogram. The solvent is removed in vacuo, the residue stirred with ice water, the insoluble product isolated by filtration, and the filter cake washed with cold water and dried. The compound has the formula

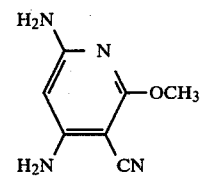

and is in the form of a yellow crystalline powder (m.p. 174° C.).

INSTRUCTION 4

6.4 parts of 2-bromo-3-cyano-4,6-diaminopyridine, 14.5 parts of phenol and 2.5 parts of potassium carbonate are heated to 145° C. until no more starting substance is detectable in a thin-layer chromatogram. The mixture is poured into water and the pH is adjusted to 9 with sodium hydroxide solution. The precipitated compound of the formula

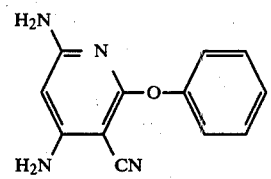

is filtered off, washed with water and dried. The yellow crystalline powder has a melting point of 176° C.

INSTRUCTION 5

4.66 parts of 6-amino-2-chloro-3-cyano-1-methyl-4-methylaminopyridinium chloride, 10 parts of alcohol, and 11.7 parts of isopropoxypropylamine are heated for 10 hours in an autoclave at 130° C. The reaction mixture is cooled, 2 parts of sodium carbonate are then added and the excess amine and the residual volatile constituents are distilled off with steam. The residue is extracted with chloroform, the extract dried with calcined sodium sulphate, and the solvent is distilled off in vacuo. The residue, which has the formula

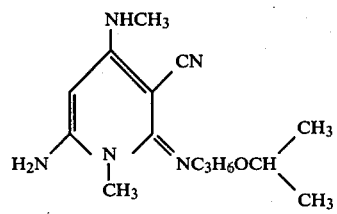

and occurs in the form of a viscous, colourless oil, is used as coupling component.

INSTRUCTION 6

4.66 parts of 6-amino-2-chloro-3-cyano-1-methyl-4-methylaminopyridinium chloride, 10 parts of alcohol, and 8.5 parts of piperidine are heated for 12 hours in an autoclave at 130° C. The reaction mixture is cooled, 2 parts of sodium carbonate are then added, and the residual constituents are distilled off with steam. The residue is extracted with chloroform. The chloroform extract is dried with calcined sodium sulphate and the solvent is then distilled off in vacuo. The residue, which has the formula

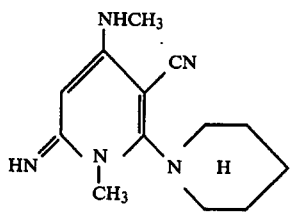

and occurs in the form of a viscous, colourless oil, is used as coupling component.

INSTRUCTION 7

4.66 parts of 6-amino-2-chloro-3-cyano-1-methyl-4-methylaminopyridinium chloride, and 12 parts of aniline are heated for 12 hours to 160° C.–170° C. The reaction mixture is cooled, 4 parts of sodium carbonate are then added, and the excess amine is distilled off with steam. The precipitated product is filtered off, washed neutral with cold water, and dried. The slightly brownish powder, which has the formula

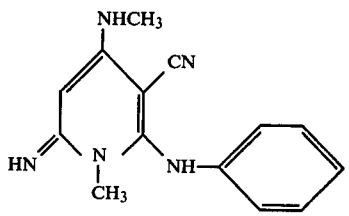

is used as coupling component.

INSTRUCTION 8

7 parts of 6-amino-2-chloro-3-cyano-1-methyl-4-methylaminopyridinium chloride, 21 parts of phenol, and 3.5 parts of potassium carbonate are heated for 24 hours to 160°–170° C. The reaction mixture is cooled, then made alkaline to phenolphthalein with 2 normal sodium hydroxide solution, and the precipitated product is filtered off, washed with water, and dried. The brown powder is extracted hot with acetone. The extract is isolated and the solvent is distilled off in vacuo. The residue, which has the formula

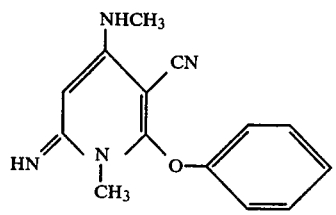

and occurs in the form of a slightly brownish powder, is used as coupling component.

INSTRUCTION 9

62.4 parts of cyanoacetic methoxypropylamide are dissolved in 125 parts by volume of chloroform and 61.4 parts of phosphoroxy chloride are added dropwise at 50° to 55° C. The mixture is refluxed for 12 hours, then the solvent is distilled off in vacuo and the residue is treated with 30 parts by volume of methyl alcohol. The viscous mass is stirred at 0° C. for 3 to 4 hours until crystallisation is terminated. The product is filtered off, washed with a small quantity of methyl alcohol, and thoroughly squeezed. The resulting slightly yellowish crystals (m.p. 160°–165° C.), which have the formula

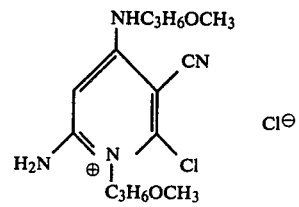

are used for manufacturing the coupling components.

INSTRUCTION 10

66.4 parts of cyanoacetic cyclohexylamide are dissolved in 200 parts by volume of chloroform and 61.4 parts of phosphoroxy chloride are added dropwise at 50° to 55° C. The mixture is refluxed for 12 hours, then the solvent is distilled off in vacuo. The residue is treated with 100 parts by volume of methyl alcohol, stirred for 2 to 3 hours, then the crystallised product is filtered off and washed with cold methyl alcohol. The pale yellow product, which is crystallised from methyl alcohol, has a melting point of 195°–196° C. and has the formula

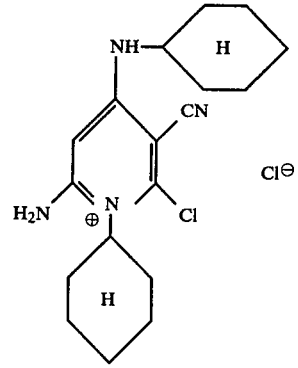

It is used for manufacturing the coupling components.

INSTRUCTION 11

75.2 parts of cyanoacetic phenylethylamide are dissolved in 200 parts by volume of chloroform and 61.4 parts of phosphoroxy chloride are added dropwise to the solution at 50° to 55° C. The mixture is refluxed for 12 hours, then the solvent is distilled off in vacuo. The residue is treated with 30 parts by volume of methyl alcohol, stirred for 3 hours at 5° to 10° C., then the crystallised product is filtered off and washed with cold methyl alcohol. The pale yellow product, which is recrystallised from methyl alcohol, has a melting point of 234°–235° C. and has the formula

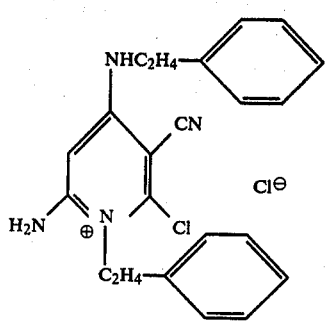

It is used for the manufacture of the coupling components.

INSTRUCTION 12

10.5 parts of 6-amino-2-chloro-3-cyano-1-methoxypropyl-4-methoxypropylaminopyridinium chloride, 15 parts of alcohol, and 26.6 parts of 35% methalamine solution are heated for 12 hours in an autoclave to 170° C. The reaction mixture is cooled, 3 parts of sodium carbonate are then added, and the excess amine and the residual volatile constituents are distilled off with steam. The residue is extracted with chloroform, the chloroform extract dried with calcined sodium sulphate, and the solvent is distilled off in vacuo. The residue, which has the formula

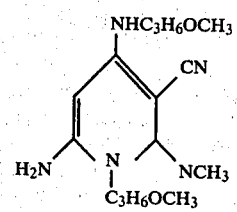

and occurs in the form of a viscous oil, is used as coupling component.

INSTRUCTION 13

9.8 parts of cyanoacetic methylamide are dissolved warm in 50 parts by volume of chloroform. The solution is then cooled and 28.7 parts of phosphoroxy bromide are added. The reaction mixture is slowly warmed to 60° C. and refluxed for 12 hours. The suspension is cooled to 0° to 5° C. and the product is filtered off. The residue is recrystallised from methyl alcohol. The yellow product, which has a melting point of 242°–244° C. and has the formula

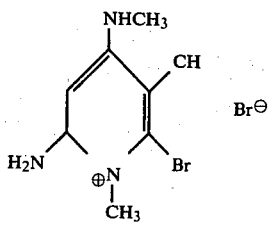

can be reacted with nucleophilic agents in analogous manner to the chlorine product to give coupling components.

EXAMPLE 1

17.2 parts of 2-chloro-4-nitroaniline are made into a paste with 39 parts by volume of conc. hydrochloric acid and stirred into a mixture of 400 parts of ice and water. The suspension is diazotised at 0° to 5° C. with 25 parts by volume of 4 N sodium nitrite solution. The diazo solution is added to a solution of 17.7 parts of 2-ethylamino-3-cyano-4,6-diaminopyridine (obtained according to Example 1) in 100 parts of alcohol. Upon completion of the coupling, the dyestuff of the formula

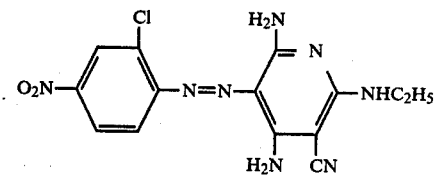

is filtered off, washed and dried. It dyes polyester fibres in brilliant orange shades which have excellent fastness properties.

EXAMPLE 2

1.5 parts of sodium nitrite are sprinkled into 18 parts of conc. sulphuric acid at 0°–10° C. The mixture is heated to 65° C. until all is dissolved, then cooled to 0° C. and treated dropwise with 20 parts by volume of a mixture of 4 parts of glacial acetic acid and 1 part of propionic acid. To the resulting solution is added dropwise a solution of 2.9 parts of 2-amino-5-nitrothiazole in 20 parts by volume of a mixture of glacial acetic acid and propionic acid (4:1) and stirring of the reaction mixture is continued for 3 hours at 0°–5° C. To this diazo solution are added 1.5 parts of urea in small amounts. The so obtained diazo solution is added to a solution of 5 parts of 2-isopropoxypropylamino-3-cyano-4,6-diaminopyridine in 20 parts of alcohol. Stirring of the mixture is continued for 5 hours and it is then diluted with ice water. The precipitated dyestuff is filtered off, washed with water and dried. The dyestuff corresponds to the formula

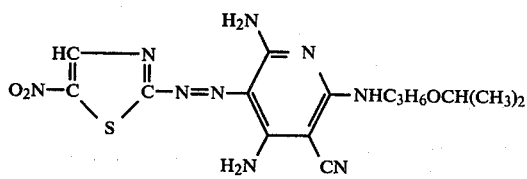

and dyes polyester and cellulose acetate fibres in bluish red shades which have very good fastness-properties.

EXAMPLE 3

3.54 parts of 5-amino-3-phenyl-1,2,4-thiadiazole are dissolved in 20 parts by volume of formic acid. At 0° to 5° C. 1.4 parts of sodium nitrite are added and the mixture is stirred for 30 minutes. When 0.05 part of sulphamic acid is added. Subsequently 6.36 parts of 2,4-bis-isopropylamino-3-cyano-6-n-hexoxypyridine are added and the mixture is rinsed with 10 parts by volume of formic acid. The mixture is heated slowly to 60° C. and stirred for 2 hours at this temperature. The paste is diluted with 300 parts of water, thoroughly stirred, sucked off and the filter cake washed with water. The dyestuff of the formula

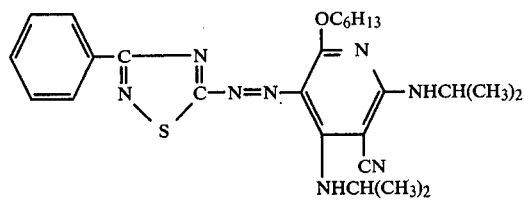

is obtained. It dyes polyester fibres in yellow shades which have very good fastness properties.

The dyestuffs listed in the following Table are obtained in analogous manner. They dye polyester fibres in the shades indicated in the last column.

Table

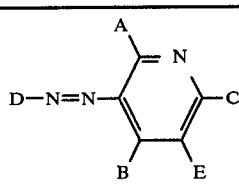

| No | D | A | B | C | E | Farb-ton |
|---|---|---|---|---|---|---|
| 1 | 2,6-dichloro-4-nitrophenyl | $NH_2$ | $NH_2$ | $NHC_6H_{13}$ | CN | scarlet |
| 2 | 4-chloro-2-cyanophenyl | $NH_2$ | $NH_2$ | $NHC_8H_{17}$ | CN | orange |
| 3 | 2-chloro-4-nitrophenyl | $NH_2$ | $NH_2$ | piperidino (N H) | CN | scarlet |
| 4 | -phenyl-1,3,4-thiadiazolyl-2 | $NH_2$ | $NH_2$ | $NHC_6H_5$ | CN | golden yellow |
| 5 | 2-bromo-6-methoxy-4-nitrophenyl | $NH_2$ | $NH_2$ | $NHC_2H_4C_6H_5$ | CN | scarlet |
| 6 | 5-chloro-2-phenoxy-phenyl | $NH_2$ | $NH_2$ | $NH_2$ | CN | yellow |
| 7 | 4-phenylazophenyl | $NH_2$ | $NH_2$ | $N(C_2H_4OCOCH_3)_2$ | CN | orange |
| 8 | 6-nitrobenzthiazolyl-2 | $NH_2$ | $NH_2$ | $NHCH_3$ | CN | orange |
| 9 | 4-nitrophenyl | $NH_2$ | $NH_2$ | $NHC_6H_5$ | CN | orange |
| 10 | 2,4,6-tribromophenyl | $NH_2$ | $NH_2$ | $OC_6H_{13}$ | CN | yellow |
| 11 | 2,4-dinitrophenyl | $NH_2$ | $NH_2$ | piperidino (N H) | CN | red |
| 12 | 4-(2'-hydroxy-5'-methylphenyl)azophenyl | $NHCH(CH_3)_2$ | $NHCH(CH_3)_2$ | $NHCH(CH_3)_2$ | CN | scarlet |
| 13 | 5-thiocyanothiazolyl-2 | $NH_2$ | $NH_2$ | $SC_6H_5$ | CN | golden yellow |
| 14 | 2,6-dibromo-4-nitrophenyl | $NH_2$ | $NH_2$ | $NHC_4H_9$ | CN | scarlet |
| 15 | 4-butylsulphonylphenyl | $NH_2$ | $NH_2$ | $OC_6H_5$ | CN | yellow |
| 16 | 3-nitro-4-phenylaminophenyl | $NH_2$ | $NH_2$ | piperidino (N H) | CN | orange |
| 17 | 4(2'-benzthiazolyl)azo-3-chlorophenyl | $NH_2$ | $NH_2$ | $N(CH_3)_2$ | CN | orange |
| 18 | 2-methylsulphonyl-4-nitrophenyl | $NHC_3H_7$ | $SCH_3$ | $NH_2$ | CN | orange |
| 19 | 2-bromo-4-nitrophenyl | $SCH_3$ | $NHC_2H_5$ | $NHC_2H_5$ | CN | orange |
| 20 | 3-methyl-1,2,4-thiadiazolyl-5- | $NH_2$ | $NH_2$ | c-cyclohexyl | CN | yellow |
| 21 | 2-methyl-4-nitrophenyl | $NH_2$ | $NH_2$ | $NHC_6H_4Cl(m)$ | CN | golden yellow |
| 22 | 2,5-dichloro-4-dimethylamino-sulphonylphenyl | $NH_2$ | $NH_2$ | $OCH(CH_3)_2$ | CN | yellow |
| 23 | 5-nitro-2,1-benzisothiazolyl-3- | $OCH_3$ | $NHCH(CH_3)_2$ | $NHCH(CH_3)_2$ | CN | reddish violet |
| 24 | 2-chloro-4-nitrophenyl | $NH_2$ | $NH_2$ | $NHC_4H_9$ | CN | orange |
| 25 | 4-diphenyl | $NH_2$ | $NH_2$ | morpholino (—N H O) | CN | yellow |
| 26 | 2,5-dichloro-4-nitrophenyl | $NH_2$ | $NH_2$ | $NHC_3H_6OCH_3$ | CN | orange |
| 27 | 4-acetylphenyl | $NH_2$ | $NHC_6H_5$ | $NHC_6H_5$ | CN | golden yellow |
| 28 | 1-naphthyl | $NH_2$ | $NH_2$ | $OCH_3$ | CN | golden yellow |

Table-continued

| No | D | A | B | C | E | Farbton |
|----|---|---|---|---|---|---------|
| 29 | 3-methyl-4-nitro-1,2-isothiazolyl-5- | NH$_2$ | NH$_2$ | NHC$_8$H$_{17}$ | CN | deep purplish red |
| 30 | 2,6-dichloro-4-nitrophenyl | NH$_2$ | NH$_2$ | piperidin-1-yl | CN | scarlet |
| 31 | 2,6-dichloro-4-ethylsulphonylphenyl | piperidin-1-yl | N(CH$_3$)$_2$ | N(CH$_3$)$_2$ | CN | scarlet |
| 32 | 4-ethoxyethoxycarbonylphenyl | NH$_2$ | NH$_2$ | OC$_6$H$_4$CH$_3$(p) | CN | yellow |
| 33 | 4-(4'-nitrophenyl)azophenyl | NH$_2$ | NH$_2$ | NHC$_3$H$_6$OC$_2$H$_5$ | CN | orange |
| 34 | 5,6-dichlorobenzthiazolyl-2 | NH$_2$ | NH$_2$ | NHCH(CH$_3$)(C$_2$H$_5$) | CN | orange |
| 35 | 4-cyanophenyl | SC$_6$H$_5$ | NHCH(CH$_3$)$_2$ | NHCH(CH$_3$)$_2$ | CN | golden yellow |
| 36 | 2-methoxy-4-nitrophenyl | NH$_2$ | NH$_2$ | NHCH$_2$(pyridyl) | CN | orange |
| 37 | 4-aminosulphonylphenyl | NH$_2$ | NH$_2$ | OC$_8$H$_{17}$ | CN | golden yellow |
| 38 | 4(3'-pyridyl)azo-3-methylphenyl | NH$_2$ | piperidin-1-yl | piperidin-1-yl | CN | orange |
| 39 | 5-chloroindazolyl-3 | NH$_2$ | NH$_2$ | NHCH$_2$C$_6$H$_5$ | CN | orange |
| 40 | 2-cyano-4-nitrophenyl | NH$_2$ | NH$_2$ | piperidin-1-yl | CN | scarlet |
| 41 | 2,4,6-trichlorophenyl | NH$_2$ | NH$_2$ | OC$_2$H$_4$OH | CN | yellow |
| 42 | 4-benzoylphenyl | NH$_2$ | NH$_2$ | NHC$_6$H$_4$C$_2$H$_5$(p) | CN | yellow |
| 43 | 2-cyano-4-nitrophenyl | NH$_2$ | NH$_2$ | NHC$_2$H$_4$COOC$_2$H$_5$ | CN | scarlet |
| 44 | 2,5-bis-methoxycarbonylphenyl | NH$_2$ | NH$_2$ | NHC$_6$H$_4$Br(p) | CN | golden yellow |
| 45 | 1-methyl-4-nitroimidazolyl-5 | NH$_2$ | NH$_2$ | N(C$_4$H$_9$)$_2$ | CN | scarlet |
| 46 | 2,4-dinitrophenyl | N(CH$_3$)$_2$ | N(CH$_3$)$_2$ | N(CH$_3$)$_2$ | CN | deep purplish red |
| 47 | 2-chloro-5-methoxy-4-nitrophenyl | NH$_2$ | NH$_2$ | NHC$_2$H$_4$Cl | CN | orange |
| 48 | 4-chloro-2-trifluoromethylphenyl | NH$_2$ | NH$_2$ | SC$_6$H$_3$Cl$_2$(2,5) | CN | yellow |
| 49 | 4[4'-(4''-nitrophenyl)azo-5'-hydroxy-3'-methyl]-1'-pyrazolylphenyl | NH$_2$ | NH$_2$ | NHC$_4$H$_9$ | CN | scarlet |
| 50 | 5-methylisoxazolyl-3 | NH$_2$ | NH$_2$ | NHC$_6$H$_4$Cl(m) | CN | yellow |
| 51 | 2-cyano-4,6-dinitrophenyl | NH$_2$ | NH$_2$ | NHC$_3$H$_6$OC$_2$H$_5$ | CN | deep purplish red |
| 52 | 4-N-propyl-phthalimidophenyl | NH$_2$ | NH$_2$ | N(C$_2$H$_4$OH)$_2$ | CN | yellow |
| 53 | 4-butylaminocarbonyl-phenyl | NH$_2$ | NH$_2$ | OC$_6$H$_4$CH$_3$(m) | CN | yellow |
| 54 | 4-phenylazo-2-nitrophenyl | NH$_2$ | NH$_2$ | NHC$_3$H$_6$OCH(CH$_3$)$_2$ | CN | scarlet |

Table-continued

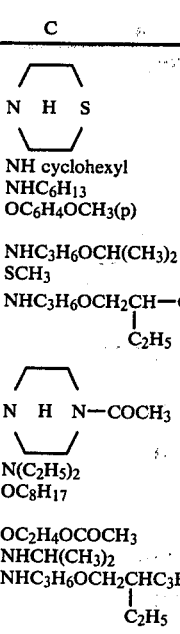

| No | D | A | B | C | E | Farbton |
|----|---|---|---|---|---|---------|
| 55 | 1-anthraquinonyl | $NH_2$ | $NH_2$ | (N H S ring) | CN | scarlet |
| 56 | 3-methyl-pyrazolyl-5 | $NH_2$ | $NH_2$ | NH cyclohexyl | CN | yellow |
| 57 | 2,4-dinitrophenyl | $NH_2$ | $NH_2$ | $NHC_6H_{13}$ | CN | red |
| 58 | 4-phenoxycarbonylphenyl | $NH_2$ | $NH_2$ | $OC_6H_4OCH_3(p)$ | CN | golden yellow |
| 59 | 3-chloro-2-methylthiophenyl | $NH_2$ | $NHC_3H_6OCH(CH_3)_2$ | $NHC_3H_6OCH(CH_3)_2$ | CN | yellow |
| 60 | 4-hexylaminosulfonylphenyl | $NH_2$ | $NH_2$ | $SCH_3$ | CN | yellow |
| 61 | 3-pyridyl | $NH_2$ | $NH_2$ | $NHC_3H_6OCH_2CH(C_2H_5)\text{—}C_3H_6CH_3$ | CN | yellow |
| 62 | 2,4,6-trinitrophenyl | $NH_2$ | $NH_2$ | (N H N—$COCH_3$ ring) | CN | deep purplish red |
| 63 | 2-cyano-4-nitrophenyl | $OC_6H_5$ | $N(C_2H_5)_2$ | $N(C_2H_5)_2$ | CN | scarlet |
| 64 | 2,6-dichloro-4-piperidino-sulphonylphenyl | $NH_2$ | $NH_2$ | $OC_8H_{17}$ | CN | golden yellow |
| 65 | 2-methylbenztriazolyl-4 | $NH_2$ | $NH_2$ | $OC_2H_4OCOCH_3$ | CN | yellow |
| 66 | 2-chloro-4-nitrophenyl | NH cyclohexyl | $NHCH(CH_3)_2$ | $NHCH(CH_3)_2$ | CN | scarlet |
| 67 | 2,6-dicyano-4-nitrophenyl | $NH_2$ | $NH_2$ | $NHC_3H_6OCH_2CH(C_2H_5)C_3H_6CH_3$ | CN | deep purplish red |
| 68 | 2,4-dinitro-6-chlorophenyl | $NH_2$ | $NH_2$ | $NHC_2H_4OH$ | CN | deep purplish red |
| 69 | 3-phenoxysulphonylphenyl | $NH_2$ | $NH_2$ | $OC_6H_4Cl(o)$ | CN | yellow |
| 70 | 2,6-dibromo-4-nitrophenyl | $NH_2$ | $NH_2$ | $NHCH_2CH_2CCOH$ | CN | scarlet |
| 71 | 1-benzyloxycarbonylphenyl | $NH_2$ | $NH_2$ | $SC_6H_{13}$ | CN | yellow |
| 72 | 1-phenylpyrazolyl-5 | $NH_2$ | $NH_2$ | $NHCH(CH_3)(C_2H_5)$ | CN | yellow |
| 73 | 2-methoxy-4-nitrophenyl | $NHC_4H_9$ | $NHC_2H_5$ | $NHC_2H_5$ | CN | scarlet |
| 74 | 2-bromo-6-cyano-4-nitro phenyl | $NH_2$ | $NH_2$ | $N(C_4H_9)_2$ | CN | deep purplish red |
| 75 | 4-pyrrolidinocarbonyl-phenyl | $NH_2$ | $NH_2$ | $OC_6H_3(CH_3)_2(m.p)$ | CN | yellow |
| 76 | 4(4'-chlorophenyl)azo-2-methoxy-5-methylphenyl | $NH_2$ | $NH_2$ | $OC_6H_5$ | CN | scarlet |
| 77 | 2,4-dinitrophenyl | $NH_2$ | $NH_2$ | $NHCH_2CON(CH_3)_2$ | CN | scarlet |
| 78 | 4-methylsulphonylbenz-thiazolyl-2 | $NH_2$ | $NH_2$ | $N(C_3H_7)_2$ | CN | orange |
| 79 | 2-ethoxycarbonyl-4-nitrophenyl | $NH_2$ | $NH_2$ | $OC_4H_9$ | CN | golden yellow |
| 80 | 2,6-dibromo-4-cyanophenyl | $NH_2$ | $NH_2$ | $NHC_3H_6OCH_2CH(C_2H_5)C_4H_9$ | CN | orange |
| 81 | 5-nitro-7-bromo-2,1-benz-isothiazolyl-3 | $NH_2$ | $NH_2$ | $NHC_5H_{11}$ | CN | violet |
| 82 | 4-nitro-2-trifluoromethyl phenyl | $NH_2$ | $NH_2$ | $NHC_6H_4CH_3(p)$ | CN | scarlet |
| 83 | 4-nitro-2-thiocyanophenyl | $NH_2$ | $NH_2$ | $OC_2H_4C_6H_5$ | CN | orange |
| 84 | quinolino-8 | $NH_2$ | $NH_2$ | $NHC_2H_4OC_6H_5$ | CN | orange |
| 85 | 5-acetyl-3-nitrothio-phenyl-2 | $NH_2$ | $NH_2$ | (N H ring) | CN | deep purplish |
| 86 | 4-ethoxy-2-nitrophenyl | $NH_2$ | $NH_2$ | $NHC_2H_4C_6H_5$ | CN | orange |
| 87 | 4-methyl-2-nitrophenyl | $NH_2$ | $NH_2$ | $OC_3H_7$ | CN | yellow |
| 88 | 5-chloro-2,1-benzisothiazol | $NH_2$ | $NH_2$ | (N H C ring) | CN | deep purplish |
| 89 | 4-propoxycarbonylphenyl | $NHC_6H_5$ | $NHC_2H_5$ | $NHC_2H_5$ | CN | orange |

Table-continued

D—N=N—[pyridine: A, B, C, E substituents]

| No | D | A | B | C | E | Farbton |
|----|---|---|---|---|---|---------|
| 90 | 2,4-dicyanophenyl | NH$_2$ | NH$_2$ | NH cyclohexyl | CN | orange |
| 91 | 2,4,5-trichlorophenyl | NH$_2$ | NH$_2$ | NHC$_2$H$_4$CN | CN | yellow |
| 92 | 4-chloro-3-nitrophenyl | NH$_2$ | NH$_2$ | OCH$_3$ | CN | yellow |
| 93 | 3-phenyl-1,2,4-thiadiazolyl-3 | NH$_2$ | NH$_2$ | NHC$_6$H$_{13}$ | CN | golden yellow |
| 94 | 2-brom-4-nitrophenyl | NH hexyl | SCH$_3$ | NH$_2$ | CN | orange |
| 95 | 2-methoxy-5-nitrophenyl | NH$_2$ | NH$_2$ | NHC$_2$H$_4$OCOCH$_3$ | CN | yellow |
| 96 | 3-butylthio-1,2,4-thiadiazolyl-5 | NH$_2$ | NH$_2$ | NHC$_3$H$_6$OCH$_3$ | CN | golden yellow |
| 97 | 3-cyano-4,5-tetramethylene-thiophenyl-2 | NH$_2$ | NH$_2$ | NHC$_6$H$_4$OCH$_3$(p) | CN | orange |
| 98 | 4-chloro-2-cyanophenyl | NHC$_6$H$_{13}$ | N(CH$_3$)$_2$ | N(CH$_3$)$_2$ | CN | orange |
| 99 | 4-cyanophenyl | NH$_2$ | NH$_2$ | NHC$_6$H$_4$OCH$_3$(o) | CN | orange |
| 100 | 5-nitro-2,1-benzisothiazolyl-3 | NH$_2$ | NH$_2$ | NHC$_3$H$_6$OCH(CH$_3$)$_2$ | CN | violet |
| 101 | 2-methyl-5-nitrophenyl | NH$_2$ | NH$_2$ | NHCH$_2$-(furfuryl) | CN | yellow |
| 102 | 5-phenyl-1,2,4-triazolyl-3 | NH$_2$ | NH$_2$ | NHC$_4$H$_8$OH | CONH$_2$ | yellow |
| 103 | 4-nitronaphthyl | NH$_2$ | NH$_2$ | NHCH$_2$-(tetrahydrofurfuryl) | CN | scarlet |
| 104 | 2,4,6-tribromophenyl | NH$_2$ | NH$_2$ | NHC$_6$H$_{13}$ | CN | yellow |
| 105 | 5-cyanothiazol-2 | NH$_2$ | NH$_2$ | NHcyclopentyl | CN | red |
| 106 | 3-phenyl-1,2,4-thiadiazolyl-5 | NHC$_2$H$_4$C$_6$H$_5$ | NHCH(CH$_3$)$_2$ | NHCM(CH$_3$)$_2$ | CN | golden yellow |
| 107 | 2,6-dichloro-4-nitrophenyl | NH$_2$ | NH$_2$ | NHC$_6$H$_{13}$ | CONH$_2$ | scarlet |
| 108 | 4-nitrophenyl | NH$_2$ | NHC$_6$H$_5$ | NHC$_6$H$_5$ | CONH$_2$ | scarlet |
| 109 | 2-bromo-6-chloro-4-nitrophenyl | N(CH$_3$)$_2$ | NHC$_2$H$_5$ | NHC$_2$H$_5$ | CONH$_2$ | red |
| 110 | 2,4-dinitrophenyl | NHC$_4$H$_9$ | N(CH$_3$)$_2$ | N(CH$_3$)$_2$ | CONH$_2$ | deep purplish red |
| 111 | 4-phenylsulphonylphenyl | NH$_2$ | NH$_2$ | NHC$_2$H$_4$N-(pyrrolidone) | CN | orange |
| 112 | 3-cyano-4-methyl-5-methoxycarbonylthiophenyl-2 | NHC$_2$H$_5$ | NHCH(CH$_3$)$_2$ | NHCH(CH$_3$)$_2$ | CONH$_2$ | bluish red |
| 113 | 4-hexoxycarbonyl-2-nitro- | NHC$_2$H$_4$OCONHC$_4$H$_9$ | N(CH$_3$)$_2$ | N(CH$_3$)$_2$ | CN | scarlet |
| 114 | 7-nitrobenzisothiazolyl-4 | NHCH$_3$ | NHcyclohexyl | NHcyclohexyl | CN | red |

EXAMPLE 4

2 parts of 6-(2',4'-dinitrophenyl)azo-4,6-diamine-2-hexylamino-3-cyanopyridine are dissolved in 9 parts of 90% sulphuric acid and the solution is stirred for 12 hours at 60° C. The solution is then allowed to cool and poured on 60 parts of ice and water. The precipitated dyestuff of the formula

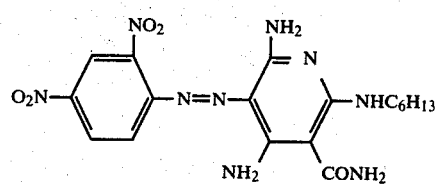

is filtered off, washed neutral with water and dried. It dyes polyester fibres in red shades which have good fastness properties.

Dyeing Instruction 1 part of the dyestuff obtained according to Example 1 is ground wet with 2 parts of a 50% aqueous solution of the sodium salt of dinapthylmethanedisulphonic acid and dried.

This dyestuff preparation is stirred with 40 parts of a 10% aqueous solution of the sodium salt of N-benzyl-6-heptadecyl-benzimidazole-disulphonic acid and 4 parts of a 40% acetic acid solution are added. A dyebath of 4000 parts by volume is prepared therefrom by dilution with water.

100 parts of a purified polyester fibre material is put into this bath at 50° C. the temperature is raised within half an hour to 120° C. to 130° C. and dyeing is carried out at this temperature for 1 hour in a closed vessel. The material is thereafter thoroughly rinsed. A full, orange dyeing of excellent fastness to light and sublimation is obtained.

EXAMPLE 5

17.2 parts of 2-chloro-4-nitroaniline are made into a paste with 39 parts by volume of conc. hydrochloric acid and this paste is then stirred into a mixture of 400 parts of ice and water. The suspension is diazotised at 0° to 5° C. with 25 parts by volume of 4K sodium nitrite solution. The diazo solution is added to a solution of 27.7 parts of the 6-amino-3-cyano-2isopropoxy-propylimino-1-methyl-4-methylamino-1,2-dihydropyridine obtained according to Instruction 1 in 150 parts of ethyl alcohol. The coupling mixture is made neutral to Congo red with sodium acetate solution. When the coupling is terminated the precipitated dyestuff, which has the formula

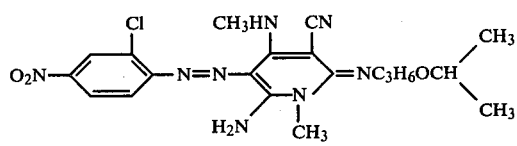

is filtered off, washed with water, and dried. It dyes polyester fibres in brilliant reddish orange shades with excellent fastness properties.

EXAMPLE 6

18.3 parts of 2,4-dinitroaniline are introduced into 55 parts of concentrated sulphuric acid and dissolved. An addition is then made dropwise at 20° of 31.8 parts of 42% nitrosylsulphuric acid, and the whole stirred for a further 2 hours at 20° to 22°. The diazo solution is added at 0° to 5° to a solution of 24.5 parts of 5-cyano-2-imino-1-methyl-4-methylamino-6-piperidino-1,2-dihydropyridine, obtained according to working example 2, in 150 parts of alcohol. The coupling mixture is stirred for 2 hours, and made neutral to Congo red with sodium acetate solution. After completion of the coupling process, the precipitated dyestuff corresponding to the formula

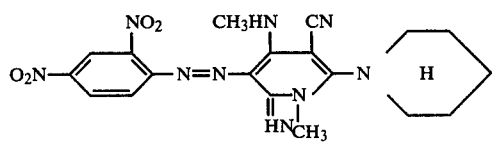

in filtered off, washed with water and finally dried. It dyes polyester fibres in red shades having very good fastness properties.

EXAMPLE 7

1.5 parts of sodium nitrite are sprinkled into 10 parts of conc. sulphuric acid at 0°–10° C. The mixture is heated to 65° C. until all is dissolved, then the solution is cooled to 0° C. and treated dropwise with 20 parts by volume of a mixture of 4 parts of glacial acetic acid and 1 part of propionic acid. A solution of 2.9 parts of 2-amino-5-nitrothiazole in 20 parts by volume of a mixture of glacial acetic acid and propionic acid (4:1) is added to the resulting solution and stirring of the reaction mixture is continued for 3 hours at 0°–5° C. To this diazo solution are added 1.5 parts of urea by small amounts. The diazo solution is added to a solution of 5.08 parts of 5-cyano-2-imino-6-phenoxy-1-methyl-4-methylamino-1,2-dihydroxypyridine in 20 parts of alcohol. The mixture is further stirred for 2 hours and then made neutral to Congo red with sodium acetate solution. When the coupling is terminated the precipitated dyestuff is filtered off, washed with water, and dried. The dyestuff, which has the formula

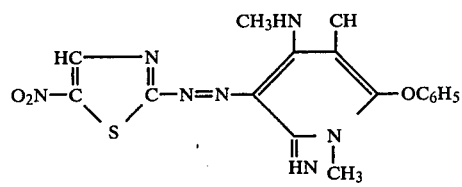

dyes polyester and cellulose acetate fibres in red shades with very good fastness properties. The dyestuffs listed in the following Table of the formula

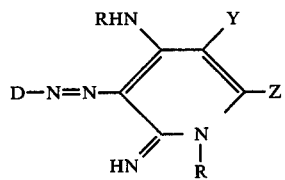

are obtained in analogous manner.

| | D | R | Z | Y | Shade on polyester fibres |
|---|---|---|---|---|---|
| 1 | 2-bromo-6-methoxy-4-nitrophenyl | CH$_3$ | SC$_6$H$_4$CH$_3$(4) | CN | golden yellow |
| 2 | 4-phenylazophenyl | C$_2$H$_4$C$_6$H$_5$ | NHC$_8$H$_{17}$ | CN | golden yellow |
| 3 | 2-chloro-4-nitrophenyl | CH$_3$ | OC$_6$H$_5$ | CN | golden yellow |
| 4 | 5-nitrothiazolyl-2 | C$_2$H$_5$ | N(C$_4$H$_9$)$_2$ | CN | bluish red |
| 5 | 3-phenyl-1,2,4-thidiazolyl-5 | C$_2$H$_5$ | NHC$_6$H$_{13}$ | CN | golden yellow |
| 6 | 2,6-dichloro-4-nitrophenyl | C$_3$H$_6$OCH$_3$ | N(CH$_3$)$_2$ | CN | scarlet |
| 7 | 5-phenyl-1,3,4-thiadiazolyl-2 | CH$_3$ | NHC$_6$H$_4$Br(4) | CN | golden yellow |
| 8 | 6-nitrobenzthiazolyl-2 | C$_3$H$_6$OC$_2$H$_5$ | NHCH$_3$ | CN | scarlet |
| 9 | 2,4,6-tribromophenyl | C$_3$H$_7$ | NH$_2$ | CN | yellow |
| 10 | 2,4-dinitrophenyl | CH$_3$ |  | CN | red |

-continued

| | D | R | Z | Y | Shade on polyester fibres |
|---|---|---|---|---|---|
| 11 | 4-(2'-hydroxy-5'-methyl-phenyl)-azophenyl | cyclopentyl | NHC$_2$H$_4$Cl | CN | scarlet |
| 12 | 4-butylsulphonylphenyl | C$_2$H$_5$ | OC$_6$H$_4$CH$_3$(3) | CN | yellow |
| 13 | 2-methoxy-4-nitrophenyl | —CH(CH$_3$)(C$_2$H$_5$) | NH-cyclophenyl | CN | orange |
| 14 | 2,6-dibromo-4-nitrophenyl | C$_3$H$_6$OCH$_3$ | NH—CH(CH$_3$)(C$_2$H$_5$) | CN | orange |
| 15 | 4-cyanophenyl | cyclohexyl | NHC$_2$H$_4$COOH | CN | golden yellow |
| 16 | 2,5-dichloro-4-dimethylamine-sulphonylphenyl | C$_2$H$_5$ | NHC$_3$H$_6$OCH$_3$ | CN | golden yellow |
| 17 | 3-nitro-4-phenylaminophenyl | C$_2$H$_4$C$_6$H$_5$ | —N(piperazinyl)NCOCH$_3$ | CN | orange |
| 18 | 3-methyl-1,2,4-thiadiazolyl-5 | CH$_2$C$_6$H$_5$ | —N(morpholinyl)O | CN | yellow |
| 19 | 2-methylsulphonyl-4-nitrophenyl | CH$_3$ | NHCH$_2$C$_6$H$_5$ | CN | scarlet |
| 20 | 2-methyl-4-nitrophenyl | C$_3$H$_6$OCH(CH$_3$)$_2$ | NHC$_4$H$_9$ | CN | orange |
| 21 | 5-nitro-2,1-benzisothiazolyl-3 | C$_2$H$_5$ | N(piperidinyl)H | CN | reddish blue |
| 22 | 4-acetylphenyl | C$_3$H$_6$OC$_2$H$_5$ | NHC$_2$H$_4$C$_6$H$_5$ | CN | yellow |
| 23 | 4-ethoxyethoxycarbonylphenyl | C$_3$H$_7$ | NHC$_6$H$_4$Cl(3) | CN | yellow |
| 24 | 3-methyl-4-nitro-1,2-isothiazolyl-5 | C$_3$H$_6$OCH$_3$ | N(CH$_3$)$_2$ | CN | red |
| 25 | 4-(4'-nitrophenyl)-azophenyl | CH$_3$ | NH-cyclohexyl | CN | orange |
| 26 | 2,6-dichloro-4-ethylsulphonyl-phenyl | CH$_3$ | N(C$_2$H$_4$OCOCH$_3$)$_2$ | CN | orange |
| 27 | 4-aminosulphonylphenyl | C$_4$H$_9$ | NHC$_6$H$_4$OCH$_3$(2) | CN | golden yellow |
| 28 | 5,6-dichlorobenzthiazolyl-2 | C$_3$H$_7$ | SC$_6$H$_3$Cl$_2$(2,5) | CN | reddish yellow |
| 29 | 5-nitroindazolyl-3 | CH$_3$ | NHC$_2$H$_4$OH | CN | orange |
| 30 | 4-benzoylphenyl | C$_2$H$_5$ | NHC$_2$H$_4$CN | CN | golden yellow |
| 31 | 2-cyano-4-nitrophenyl | C$_3$H$_7$ | N(C$_2$H$_5$)$_2$ | CN | scarlet |
| 32 | 4-N-propylphthalimido | C$_2$H$_4$C$_6$H$_5$ | NHC$_4$H$_8$OH | CN | golden yellow |
| 33 | 2,4,6-trichlorophenyl | C$_2$H$_5$ | NHCH$_3$ | CN | golden yellow |
| 34 | 4-chloro-2-trifluoromethyl-phenyl | cyclopentyl | NHCH$_2$CON(CH$_3$)$_2$ | CN | golden yellow |
| 35 | 2,5-bismethoxycarbonylphenyl | —CH(CH$_3$)(C$_2$H$_5$) | NHC$_2$H$_4$OC$_6$H$_5$ | CN | yellow |
| 36 | 2-cyano-4,6-dinitrophenyl | CH$_2$C$_6$H$_5$ | NHC$_5$H$_{11}$ | CN | bluish red |
| 37 | 1-methyl-4-nitroimidazolyl-5 | CH$_2$CH(CH$_3$)$_2$ | N(C$_3$H$_7$)$_2$ | CONH$_2$ | scarlet |
| 38 | 2-chloro-5-methoxy-4-nitro-phenyl | CH$_3$ | OC$_6$H$_3$(CH$_3$)$_2$(3,4) | CN | reddish yellow |
| 39 | 4-butylaminocarbonylphenyl | CH(CH$_3$)$_2$ | NHC$_2$H$_4$N(piperidone)H | CN | reddish yellow |
| 40 | 4-phenylazo-2-nitrophenyl | C$_2$H$_5$ | N(piperidinyl)H | CN | red |
| 41 | 5-chloro-2-methylthio-phenyl | C$_3$H$_7$ | OC$_6$H$_4$OCH$_3$(4) | CN | yellow |
| 42 | 2,4,6-trinitrophenyl | CH$_2$CH(CH$_3$)$_2$ | NHCH$_2$-(tetrahydrofuranyl) | CONH$_2$ | violet |
| 43 | 3-methylpyrazolyl-5 | C$_2$H$_5$ | NHCH$_2$-(tetrahydrofuranyl)H | CN | yellow |
| 44 | 4-phenoxycarbonylphenyl | CH$_3$ | NHC$_6$H$_4$OCH$_3$(4) | CN | golden yellow |

-continued

| | D | R | Z | Y | Shade on polyester fibres |
|---|---|---|---|---|---|
| 45 | 5-nitro-7-bromo-2,1-benzisothiazolyl-3 | $C_3H_6OCH(CH_3)_2$ | $NHC_4H_9$ | CN | reddish blue |
| 46 | 3-phenoxysulphonylphenyl | cyclohexyl | ⟨N H S⟩ | CN | yellow |
| 47 | 4-hexylaminosulphonylphenyl | $CH_3$ | $NHC_6H_5$ | CN | reddish yellow |
| 48 | 4-benzyloxycarbonylphenyl | $CH_3$ | $NHCH(CH_3)_2$ | CN | reddish yellow |
| 49 | 6-methylsulphonylbenzthiazolyl-2 | $C_6H_{13}$ | $NHC_6H_4C_2H_5(4)$ | $CONH_2$ | scarlet |
| 50 | 2,6-dicyano-4-nitrophenyl | $C_3H_7$ | $N(C_2H_5)_2$ | CN | bluish red |
| 51 | 2,4-dinitro-6-chlorophenyl | $CH_3$ | $OC_6H_5$ | CN | orange |
| 52 | 2,6-dichloro-4-piperidinosulphonylphenyl | $CH_3$ | $NHC_3H_6OCH_2CHC_4H_9$ \| $C_2H_5$ | CN | orange |
| 53 | 1-phenylpyrazolyl-5 | $CH_3$ | $SC_6H_5$ | CN | yellow |
| 54 | 4-nitro-2-trifluoromethyl | $C_2H_4C_6H_5$ | $NHC_8H_{17}$ | CN | orange |
| 55 | 3-butylthio-1,2,4-thiadiazolyl-3 | $CH_3$ | $NHCH(CH_3)_2$ | CN | yellowish orange |
| 56 | 2-bromo-6-cyano-4-nitrophenyl | $CH_3$ | $NHC_3H_6OCH(CH_3)_2$ | CN | red |
| 57 | 3-cyano-4-methyl-5-methoxycarbonyl-thiophenyl-2 | $C_2H_5$ | $NHC_6H_{13}$ | CN | bluish red |
| 58 | 2,4,5-trichlorophenyl | $CH_3$ | NH-cyclohexyl | CN | yellowish orange |
| 59 | 4-pyrrolidinocarbonylphenyl | $CH_3$ | $NHC_3H_6OC_2H_5$ | CN | yellowish orange |
| 60 | 2-methoxy-5-nitrophenyl | $C_2H_5$ | $N(C_2H_9)_2$ | CN | reddish yellow |
| 61 | 4-nitro-2-thiocyanophenyl | $CH_3$ | $N(C_2H_4OH)_2$ | CN | orange |
| 62 | 4-(4'-chlorophenyldiazo-2-methoxy-5-methylphenyl | $C_3H_6OC_2H_5$ | $NHCH_2$—⟨pyridyl⟩ | CN | scarlet |
| 63 | 4-phenylsulphonylphenyl | $CH_3$ | $NHC_3H_6OCH(CH_3)_2$ | CN | yellowish orange |
| 64 | 3-cyano-4,5-tetramethylene-thiophenyl-2 | $CH_3$ | $NHC_6H_4OCH_3(4)$ | CN | orange |
| 65 | 2-ethoxycarbonyl-4-nitrophenyl | $C_2H_5$ | $NHC_2H_5$ | CN | scarlet |
| 66 | 5-acethyl-3-nitrothiophenyl-2 | $C_2H_5$ | $NHC_6H_{13}$ | CN | bluish red |
| 67 | 5-phenyl-1,2,4-triazolyl-3 | $CH_3$ | $NHC_6H_4Br(4)$ | CN | yellow |
| 68 | 5-cyanothiazole-2 | $C_2H_5$ | $NHCH_3$ | CN | red |
| 69 | 4-ethoxy-2-nitrophenyl | $C_3H_6OC_2H_5$ | $NHC_2H_4C_6H_5$ | CN | orange |
| 70 | 2,4-dicyanophenyl | $CH_3$ | $NHC_3H_6OCH_2CHC_4H_9$ \| $C_2H_5$ | CN | orange |
| 71 | 4-methyl-2-nitrophenyl | $C_3H_7$ | $NHC_6H_4Cl(3)$ | CN | golden yellow |
| 72 | 4-propoxycarbonylphenyl | $C_2H_5$ | $NHC_3H_6OCH_3$ | CN | golden yellow |
| 73 | 2-methyl-5-nitrophenyl | $CH_2C_6H_5$ | $NHC_5H_{11}$ | CN | yellow |
| 74 | 4-nitrophenyl | $C_2H_5$ | $NHC_2H_5$ | CN | golden yellow |
| 75 | 4-hexoxycarbonyl-2-nitrophenyl | $C_3H_6OCH_3$ | $NHC_4H_9$ | CN | orange |
| 76 | 3-pyridyl | $C_6H_{13}$ | $NHC_6H_4CH_3(4)$ | CN | yellow |

EXAMPLE 8

2 parts of 5-(2',4'-dinitrophenyl)axo-4,6-diamino-2-hexylamino-3-cyanopyridine are dissolved in 9 parts of 90% sulphuric acid and the solution is stirred for 12 hours at 60° C. The solution is then allowed to cool and poured on 60 parts of ice and water. The precipitated dyestuff of the formula

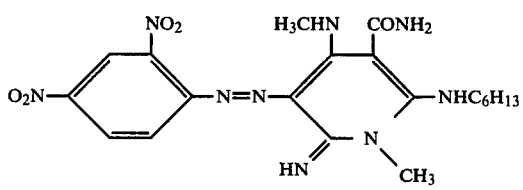

is filtered off, washed neutral with water and dried. It dyes polyester fibres in deep purplish red shades.

Dyeing Instruction 1 part of the dyestuff obtained according to Example 5 is ground wet with 2 parts of a 50% aqueous solution of the sodium salt of dinaphthylmethanedisulphonic acid and dried. This dyestuff preparation is stirred with 40 parts of a 10% aqueous solution of the sodium salt of N-benzyl-u-heptadecylbenzimidazole-disulphonic acid and 4 parts of a 40% acetic acid solution are added. A dyebath of 4000 parts by volume is prepared therefrom by dilution with water 100 parts of a cleansed polyester fibre material is put into this bath at 50° C., the temperature is raised within half an hour to 120° C. to 130° C. and dyeing is carried out at this temperature for 1 hour in a closed vessel. The material is thereafter thoroughly rinsed. A full, reddish orange dyeing of excellent fastness to light and sublimation is obtained.

I claim:

1. A disperse azo dyestuff, free from water solubilizing groups, of the formula

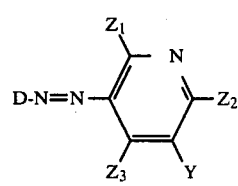

wherein

Y is —CN or —CONH$_2$, two of Z$_1$, Z$_2$ and Z$_3$ are —NR'R" and the third is —NR'R", —OR''' or —SR''', where R', R" and R''' independently represent hydrogen. alkyl of 1 to 12 carbon atoms, which is unsubstituted or substituted by:

hydroxy, cyano, carboxy, carbalkoxy of 2 to 6 carbon atoms, alkoxy of 1 to 18 carbon atoms, phenoxy, acyloxy, acylamino, phenyl or phenyl substituted by halo, lower alkyl, lower alkoxy, β-hydroxyethyl, or lower carboalkoxy; and wherein acyl is alkanoyl of up to 5 carbon atoms, alkylcarbamyl of up to 5 carbon atoms, alkoxycarbonyl of up to 5 carbon atoms, phenylcarbamyl, phenoxycarbonyl benzoyl, phenoxyacetyl, chloroacetyl or phenylacetyl;

phenyl which is unsubstituted or substituted by: chloro, bromo, fluoro; alkyl of 1 to 16 carbon atoms which is unsubstituted or substituted by bromo, chloro, lower alkoxy, cyano or lower alkoxycarbonyl; lower alkoxycarbonyl, lower alkoxysulfonyl, acetyl, aminocarbonyloxy, aminosulfonyl, lower alkylaminosulfonyl, di(lower alkyl) sulfonyl, methylsulfonyl, methylsulfinyl, methylthio, ethylthio or phenylthio;

cyclohexyl; or

R' and R" taken together with the nitrogen to which they are attached, represent piperidino, pyrrolidino, morpholino, piperazino, methylpiperazino or acetylpiperazino; and D is phenyl or phenyl substituted by: halo, hydroxy, cyano, thiocyano, nitro, lower alkyl, triflurormethyl, lower alkoxy, formyl, lower alkylcarbonyl, benzoyl, methylbenzoyl, lower alkoxycarbonyl, benzyloxycarbonyl, cyclohexyloxycarbonyl, phenoxycarbonyl, lower alkoxycarbonyloxy, benzoyloxycarbonyloxy, lower alkylcarbonyloxy, benzoyloxy, lower alkylcarbonylamino, benzoylamino, lower alkylsulfonyl, chloroethylsulfonyl, hydroxyethylsulfonyl, aminosulfonyl, lower alkylaminosulfonyl, di(lower alkyl) aminosulfonyl, di(hydroxyethyl) aminosulfonyl, phenylaminosulfonyl, (chloro- or methoxy-) phenylaminosulfonyl, benzylaminosulfonyl, N-piperidylsulfonyl, N-morpholinosulfonyl, lower alkylsulfonyloxy, cyclohexylsulfonyloxy, chloromethylsulfonyloxy, cyanoethylsulfonyloxy, phenylsulfonyloxy, aminosulfonyloxy, (chloro- or methoxy-) phenylsulfonyloxy, N-morpholinosulfonyloxy, ethyleneaminosulfonyloxy, lower (monoalkyl- or dialkyl-) aminosulfonyloxy, phenylaminosulfonyloxy, N-phenyl-N(lower alkyl) aminosulfonyloxy, N-(methoxy- or chloro-) phenyl aminosulfonyloxy, phenylamino, nitrophenylamino, dinitrophenylamino, phenyl, phenoxy or acetylaminophenyl;

phenylazophenyl which unsubstituted or substituted by: chloro, bromo, hydroxy, cyano, nitro, lower alkyl, trifluoromethyl, lower alkoxy of phenoxy;

naphthyl which is unsubstituted or substituted by: methoxy, ethoxy, phenylazo or dimethylaminosulfonyl; or D is a heterocyclic radical selected from: thiazolyl which is unsubstituted or substituted by chloro, bromo, nitro, cyano, thiocyano, lower alkyl, lower alkoxy, lower alkylmercapto, phenyl, benzyl, phenethyl, lower alkoxycarbonyl, trifluoromethyl, lower alkylcarbonyl or lower alkylsulfonyl; benzthiazolyl which is unsubstituted or substituted by chloro, bromo, cyano, thiocyano, nitro, lower alkyl, lower alkoxy, benzyl, phenethyl, lower alkylsulfonyl, phenyl, lower alkylmercapto, lower alkoxycarbonyl, lower alkylcarbonyl, trifluoromethyl, cyanoethylsulfonyl, or aminosulfonyl;

pyrazoyl which is unsubstituted or substituted by cyano, lower alkyl, lower alkoxy, lower alkoxycarbonyl or phenyl; thiadiazolyl which is unsubstituted or substituted by lower alkoxy, lower alkyl, phenyl, lower alkylsulfonyl or lower alkylmercapto;

imidazoyl which is unsubstituted or substituted by nitro, or lower alkyl;

thienyl which is unsubstituted or substituted by nitro, lower alkyl, lower alkylsulfonyl, lower alkoxycarbonyl or acetyl;

isothiazolyl or isothiazole substituted by lower alkyl, lower alkylsulfonyl, lower alkoxycarbonyl, nitro, cyano or phenyl; and benzisothiazolyl which is unsubstituted or substituted by lower alkyl, nitro or halo.

2. An azo dye as claimed in claim 1 of the formula

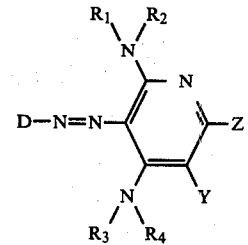

wherein R$_1$, R$_2$, R$_3$ and R$_4$ each represent hydrogen, phenyl benzyl, phenylethyl, cyclohexyl, unsubstituted C$_1$-C$_{12}$ alkyl or C$_1$-C$_{12}$ alkyl substituted by chlorine, bromine, C$_1$-C$_8$-alkoxy, hydroxy, carboxyl, C$_1$-C$_5$-alkyl-oxy-carbonyl, phenoxy, C$_1$-C$_5$-alkylcarbonyloxy, C$_1$-C$_5$-alkylcarbamyloxy, benzoyl, phenylaminocarbonyloxy, C$_1$-C$_5$-alkoxycarbonyloxy, C$_1$-C$_5$-phenoxycarbonyloxy, phenoxyacetyl, chloroacetyl or phenylacetyl, or R$_1$ and R$_2$ and/or R$_3$ and R$_4$ together and piperidine, pyrrolidine, morpholine, piperazine, or methylpiperazine and Z$_4$ is a radical of the formula

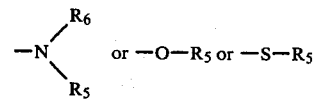

wherein R$_5$ and R$_6$ each represent hydrogen, phenyl, benzyl, phenylethyl, cyclohexyl, unsubstituted C$_1$-C$_{12}$ alkyl or C$_1$-C$_{12}$ alkyl substituted by chlorine, bromine, C$_1$-C$_8$-alkoxy, hydroxy, carboxyl, C$_1$-C$_5$-alkyl-oxycarbonyl, phenoxy, C$_1$-C$_5$-alkylcarbonyloxy, C$_1$-C$_5$-alkylcarbamyloxy, benzoyl, phenylaminocarbonyloxy, C$_1$-C$_5$-alkoxycarbonyloxy, C$_1$-C$_5$-phenoxycarbonyloxy, phenoxyacetyl, chloroacetyl or phenyl acetyl, and R$_5$ and R$_6$ together can be piperidine, pyrrolidine, morpholine, piperazine, or methylpiperazine.

3. An azo dye as claimed in claim 2, wherein Y is cyano.

4. An azo dye as claimed in claim 2, wherein R$_1$, R$_2$, R$_3$ and R$_4$ each represents hydrogen.

5. An azo dye according to claim 1, wherein D is said heterocyclic radical.

6. An azo dye according to claim 1, wherein D is said phenyl, substituted phenyl, phenylazophenyl or substituted phenylazophenyl.

7. A dyestuff as claimed in claim 4 of the formula

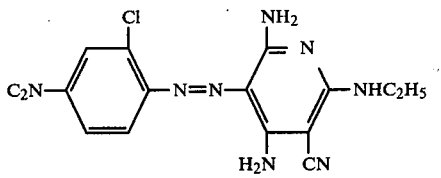

8. A dyestuff as claimed in claim 4 of the formula

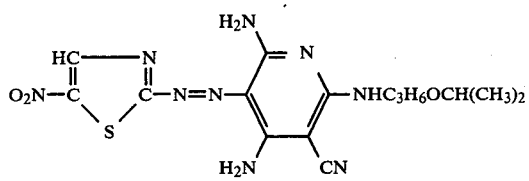

9. A dyestuff as claimed in claim 4 of the formula

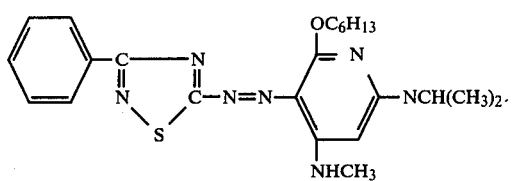

10. An azo dyestuff as claimed in claim 1 of the formula

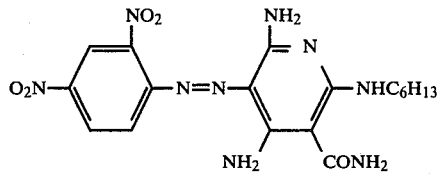

11. A disperse azo dyestuff, free from water-solubilizing groups, of the formula

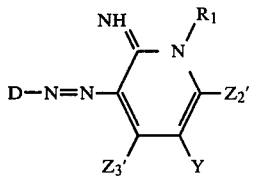

or a tautomer thereof, wherein $Z_2$ is $-NR'R'''$, $-OR'''$ or $-SR'''$; and $Z_3$ is $-NHR_1$ $R_1$ is alkyl of 1 to 12 carbon atoms which is unsubstituted or substituted by: hydroxy, cyano, carboxy, carbalkoxy of 2 to 6 carbon atoms, alkoxy of 1 to 18 carbon atoms, phenoxy, acyloxy, acylamino, or phenyl which is unsubstituted or substituted by halo, lower alkyl, lower alkoxy, β-hydroxyethyl, or lower carboalkoxy and wherein acyl is alkanoyl of up to 5 carbon atoms, alkylcarbamyl or up to 5 carbon atoms, alkoxycarbonyl of up to 5 carbon atoms, phenylcarbanyl, phenoxycarbonyl, benzoyl, phenoxyacetyl, chloroacetyl or phenylacetyl;

cyclohexyl; or phenyl which is unsubstituted or substituted by: chloro, bromo, fluoro; alkyl of 1 to 6 carbon atoms which is unsubstituted or substituted by bromo, chloro, lower alkoxy, cyano or lower alkoxycarbonyl; lower alkoxycarbonyl, lower alkoxysulfonyl, trifluoromethyl, acetyl, aminocarbonyloxy, aminosulfonyl, lower alkylaminosulfonyl, di(lower alkylamino) sulfonyl, methylsulfonyl, methylsulfinyl, methylthio, ethylthio or phenylthio;

$R'$, $R''$ and $R'''$ independently represent hydrogen; alkyl of 1 to 12 carbon atoms which is unsubstituted or substituted by:

hydroxy, cyano, carboxy, carbalkoxy of 2 to 6 carbon atoms, alkoxy of 1 to 18 carbon atoms, phenoxy, acyloxy, acylamino, or phenyl which is unsubstituted or substituted by halo, lower alkyl, lower alkoxy, β-hydroxyethyl, or lower carboalkoxy, and where acyl is alkanoyl of up to 5 carbon atoms, alkylcarbamyl of up to 5 carbon atoms, alkyloxycarbonyl of up to 5 carbon atoms, phenylcarbamyl, phenoxycarbonyl, benzoyl, phenoxyacetyl, chloroacetyl or phenylacetyl;

phenyl which is unsubstituted or substituted by: chloro, bromo, fluoro; alkyl of 1 to 6 carbon atoms which is unsubstituted or substituted by bromo, chloro, lower alkoxy, cyano or lower alkoxycarbonyl; lower alkoxycarbonyl, lower alkoxysulfonyl, acetyl, aminocarbonyloxy, aminosulfonyl, lower alkylaminosulfonyl di(lower alkyl) sulfonyl, methylsulfonyl, methylsulfinyl, methylthio, ethylthio or phenylthio;

cyclohexyl; or $R'$ and $R''$ taken together with the nitrogen to which they are attached, represent piperidino, pyrrolidino, morpholino, piperazino, methylpiperazino or acetylpiperazino; and D is phenyl or phenyl substituted by: halo, hydroxy, cyano, thiocyano, nitro, lower alkyl, trifluoromethyl, lower alkoxy, formyl, lower alkylcarbonyl, benzoyl, methylbenzoyl, lower alkoxycarbonyl, benzyloxycarbonyl, cyclohexyloxycarbonyl phenoxycarbonyl, lower alkoxycarbonyloxy, benzoyloxycarbonyloxy, lower alkylcarbonyloxy, benzoyloxy, lower alkylcarbonylamino, benzoylamino, lower alkylsulfonyl, chloroethylsulfonyl, hydroxyethylsulfonyl, aminosulfonyl, lower alkylaminosulfonyl, di(lower alkyl) aminosulfonyl, di(hydroxyethyl) aminosulfonyl, phenylaminosulfonyl, (chloro- or methoxy-) phenylaminosulfonyl, benzylaminosulfonyl, N-piperidylsulfonyl, N-morpholinosulfonyl, lower alkylsulfonyloxy, cyclohexylsulfonyloxy, chloromethylsulfonyloxy, cyanoethylsulfonyloxy, phenylsulfonyloxy, aminosulfonyloxy, (chloro- or methody-) phenylsulfonyl N-morpholinosulfonyloxy, ethyleneiminosulfonyloxy, lower (monoalkyl- or dialkyl) aminosulfonyloxy phenylaminosulfonyloxy, N-phenyl-N(lower alkyl) aminosulfonyloxy, N-(methoxy- or chloro-) phenyl aminosulfonyloxy, phenylamino, nitrophenylamino, dinitrophenylamino, phenyl, phenoxy or acetylaminophenyl;

phenylazophenyl which is unsubstituted or substituted by: chloro, bromo, hydroxy, cyano, nitro, lower alkyl, trifluoromethyl, lower alkoxy or phenoxy;

naphthyl which is unsubstituted or substituted by: methoxy, ethoxy, phenylazo or dimethylaminosulfonyl; or D is a heterocyclic radical selected from: thiazolyl which is unsubstituted or substituted by chloro, bromo, nitro, cyano, thiocyano, lower alkyl, lower alkoxy, lower alkylmercapto, phenyl, benzyl, phenethyl, lower alkoxycarbonyl, trifluoromethyl, lower alkylcarbonyl or lower alkylsulfonyl; benzthiazolyl which is unsubstituted or substituted bhy chloro, bromo, cyano, thiocyano, nitro, lower alkyl, lower alkoxy, benzyl, phenethyl, lower alkylsulfonyl, phenyl, lower alkylmercapto, lower alkoxycarbonyl, lower alkylcarbonyl, trifluoromethyl, cyanoethylsulfonyl, or aminosulfonyl;

pyrazoyl which is unsubstituted or substituted by cyano, lower alkyl, lower alkoxy, lower alkoxycarbon or phenyl;

thiadiazolyl which is unsubstituted or substituted by lower alkoxy, lower alkyl, phenyl, lower alkylsulfonyl, or lower alkylmercapto;

imidazoyl which is unsubstituted or substituted by nitro or lower alkyl;

thienyl which is unsubstituted or substituted by nitro, lower alkyl, lower alkylsulfonyl, lower alkoxycarbonyl or acetyl;

isothiazolyl or isothiazole substituted by lower alkyl, lower alkylsulfonyl, lower alkoxycarbonyl, nitro, cyano or phenyl; and benzisothiazolyl which is unsubstituted or substituted by lower alkyl, nitro or halo.

12. An azo dyestuff according to claim 11, wherein $R_1$ is said alkyl or substituted alkyl or cyclohexyl.

13. An azo dyestuff according to claim 11, wherein $Z_2$ is —NHR'.

14. An azo dyestuff according to claim 11, wherein $Z_2$ is —OR''' or —SR'''.

15. An azo dyestuff according to claim 14, wherein $Z_2$ is —OR''' and R''' is said phenyl or substituted phenyl.

16. An azo dyestuff according to claim 11 of the formula

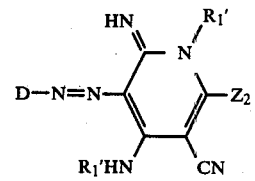

or a tautomer thereof wherein $Z_2$ is —NR'R''.

17. An azo dyestuff according to claim 11, wherein D is said heterocyclic radical.

18. An azo dyestuff according to claim 11, wherein D is said phenyl, substituted phenyl, phenylazophenyl or substituted phenylazophenyl.

19. A dyestuff as claimed in claim 18 of the formula

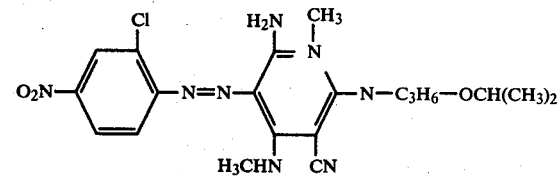

20. An azo dyestuff according to claim 11, wherein Y represents a cyano group.

* * * * *